(12) United States Patent
Kim et al.

(10) Patent No.: US 11,268,078 B1
(45) Date of Patent: Mar. 8, 2022

(54) NUCLEIC ACID-GUIDED NICKASES

(71) Applicant: Inscripta, Inc., Boulder, CO (US)

(72) Inventors: Juhan Kim, Boulder, CO (US); Benjamin Mijts, Boulder, CO (US)

(73) Assignee: Inscripta, Inc., Boulder, CO (US)

(*) Notice: Subject to any disclaimer, the term of this patent is extended or adjusted under 35 U.S.C. 154(b) by 0 days.

(21) Appl. No.: 17/463,581

(22) Filed: Sep. 1, 2021

Related U.S. Application Data

(60) Provisional application No. 63/133,502, filed on Jan. 4, 2021.

(51) Int. Cl.
*C12N 9/22* (2006.01)
*C12N 15/11* (2006.01)
*C12N 15/90* (2006.01)

(52) U.S. Cl.
CPC ............... *C12N 9/22* (2013.01); *C12N 15/11* (2013.01); *C12N 15/907* (2013.01); *C12Y 301/21004* (2013.01); *C12N 2310/20* (2017.05); *C12N 2800/80* (2013.01)

(58) Field of Classification Search
None
See application file for complete search history.

(56) References Cited

PUBLICATIONS

Parks et al. (A standardized bacterial taxonomy based on genome phylogeny substantially revises the tree of life, Nat. Biotechnol. 36:996-1004(2018)).*

* cited by examiner

*Primary Examiner* — Suzanne M Noakes
*Assistant Examiner* — Jae W Lee
(74) *Attorney, Agent, or Firm* — Sarah Brashears

(57) ABSTRACT

The present disclosure provides engineered nucleic acid-guided nickases and optimized scaffolds for making rational, direct edits to nucleic acids in live cells.

30 Claims, 16 Drawing Sheets

Specification includes a Sequence Listing.

SEQUENCE LISTING

```
<160> NUMBER OF SEQ ID NOS: 32

<210> SEQ ID NO 1
<211> LENGTH: 1367
<212> TYPE: PRT
<213> ORGANISM: Streptococcus acidominimus

<400> SEQUENCE: 1

Met Thr Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Ala Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
```

```
            225                 230                 235                 240
        Phe Leu Lys Leu Ile Val Gly Asn Gln Ala Asp Phe Lys Lys Tyr Phe
                        245                 250                 255

Asn Leu Asp Glu Lys Ala Ser Leu His Phe Ser Lys Glu Ser Tyr Asp
                        260                 265                 270

Glu Asp Leu Glu Thr Leu Leu Gly Tyr Ile Gly Asp Asp Tyr Ser Asp
                        275                 280                 285

Val Phe Leu Lys Ala Lys Lys Leu Tyr Asp Ala Ile Leu Leu Ser Gly
        290                 295                 300

Ile Leu Thr Val Thr Asp Asn Gly Thr Glu Thr Pro Leu Ser Ser Ala
        305                 310                 315                 320

Met Ile Met Arg Tyr Lys Glu His Glu Glu Asp Leu Gly Leu Leu Lys
                        325                 330                 335

Ala Tyr Ile Arg Asn Ile Ser Leu Lys Thr Tyr Asn Glu Val Phe Asn
                        340                 345                 350

Asp Asp Thr Lys Asn Gly Tyr Ala Gly Tyr Ile Asp Gly Lys Thr Asn
                        355                 360                 365

Gln Glu Asp Phe Tyr Val Tyr Leu Lys Lys Leu Leu Ala Lys Phe Glu
                        370                 375                 380

Gly Ala Asp Tyr Phe Leu Glu Lys Ile Asp Arg Glu Asp Phe Leu Arg
        385                 390                 395                 400

Lys Gln Arg Thr Phe Asp Asn Gly Ser Ile Pro Tyr Gln Ile His Leu
                        405                 410                 415

Gln Glu Met Arg Ala Ile Leu Asp Lys Gln Ala Lys Phe Tyr Pro Phe
                        420                 425                 430

Leu Ala Lys Asn Lys Glu Arg Ile Glu Lys Ile Leu Thr Phe Arg Ile
                        435                 440                 445

Pro Tyr Tyr Val Gly Pro Leu Ala Arg Gly Asn Ser Asp Phe Ala Trp
        450                 455                 460

Ser Ile Arg Lys Arg Asn Glu Lys Ile Thr Pro Trp Asn Phe Glu Asp
        465                 470                 475                 480

Val Ile Asp Lys Glu Ser Ser Ala Glu Ala Phe Ile Asn Arg Met Thr
                        485                 490                 495

Ser Phe Asp Leu Tyr Leu Pro Glu Glu Lys Val Leu Pro Lys His Ser
                        500                 505                 510

Leu Leu Tyr Glu Thr Phe Thr Val Tyr Asn Glu Leu Thr Lys Val Arg
                        515                 520                 525

Phe Ile Ala Glu Gly Met Ser Asp Tyr Gln Phe Leu Asp Ser Lys Gln
                        530                 535                 540

Lys Lys Asp Ile Val Arg Leu Tyr Phe Lys Gly Lys Arg Lys Val Lys
        545                 550                 555                 560

Val Thr Asp Lys Asp Ile Ile Glu Tyr Leu His Ala Ile Asp Gly Tyr
                        565                 570                 575

Asp Gly Ile Glu Leu Lys Gly Ile Glu Lys Gln Phe Asn Ser Ser Leu
                        580                 585                 590

Ser Thr Tyr His Asp Leu Leu Asn Ile Ile Asn Asp Lys Glu Phe Leu
                        595                 600                 605

Asp Asp Ser Ser Asn Glu Ala Ile Ile Glu Glu Ile Ile His Thr Leu
                        610                 615                 620

Thr Ile Phe Glu Asp Arg Glu Met Ile Lys Gln Arg Leu Ser Lys Phe
        625                 630                 635                 640

Glu Asn Ile Phe Asp Lys Ser Val Leu Lys Lys Leu Ser Arg Arg His
                        645                 650                 655
```

```
Tyr Thr Gly Trp Gly Lys Leu Ser Ala Lys Leu Ile Asn Gly Ile Arg
            660                 665                 670

Asp Glu Lys Ser Gly Asn Thr Ile Leu Asp Tyr Leu Ile Asp Asp Gly
            675                 680                 685

Ile Ser Asn Arg Asn Phe Met Gln Leu Ile His Asp Asp Ala Leu Ser
            690                 695                 700

Phe Lys Lys Lys Ile Gln Lys Ala Gln Ile Ile Gly Asp Lys Asp Lys
705                 710                 715                 720

Asp Asn Ile Lys Glu Val Val Lys Ser Leu Pro Gly Ser Pro Ala Ile
                725                 730                 735

Lys Lys Gly Ile Leu Gln Ser Ile Lys Ile Val Asp Glu Leu Val Lys
            740                 745                 750

Val Met Gly Arg Lys Pro Glu Ser Ile Val Val Glu Met Ala Arg Glu
            755                 760                 765

Asn Gln Tyr Thr Asn Gln Gly Lys Ser Asn Ser Gln Gln Arg Leu Lys
            770                 775                 780

Arg Leu Glu Glu Ser Leu Glu Glu Leu Gly Ser Lys Ile Leu Lys Glu
785                 790                 795                 800

Asn Ile Pro Ala Lys Leu Ser Lys Ile Asp Asn Asn Ser Leu Gln Asn
            805                 810                 815

Asp Arg Leu Tyr Leu Tyr Tyr Leu Gln Asn Gly Lys Asp Met Tyr Thr
            820                 825                 830

Gly Asp Asp Leu Asp Ile Asp Arg Leu Ser Asn Tyr Asp Ile Asp His
            835                 840                 845

Ile Ile Pro Gln Ala Phe Leu Lys Asp Asn Ser Ile Asp Asn Lys Val
            850                 855                 860

Leu Val Ser Ser Ala Ser Asn Arg Gly Lys Ser Asp Asp Val Pro Ser
865                 870                 875                 880

Leu Glu Val Val Lys Lys Arg Lys Thr Leu Trp Tyr Gln Leu Leu Lys
                885                 890                 895

Ser Lys Leu Ile Ser Gln Arg Lys Phe Asp Asn Leu Thr Lys Ala Glu
            900                 905                 910

Arg Gly Gly Leu Ser Pro Glu Asp Lys Ala Gly Phe Ile Gln Arg Gln
            915                 920                 925

Leu Val Glu Thr Arg Gln Ile Thr Lys His Val Ala Arg Leu Leu Asp
            930                 935                 940

Glu Lys Phe Asn Asn Lys Lys Asp Glu Asn Asn Arg Ala Val Arg Thr
945                 950                 955                 960

Val Lys Ile Ile Thr Leu Lys Ser Thr Leu Val Ser Gln Phe Arg Lys
                965                 970                 975

Asp Phe Glu Leu Tyr Lys Val Arg Glu Ile Asn Asp Phe His His Ala
            980                 985                 990

His Asp Ala Tyr Leu Asn Ala Val  Val Ala Ser Ala Leu  Leu Lys Lys
            995                 1000                1005

Tyr Pro  Lys Leu Glu Pro Glu  Phe Val Tyr Gly Asp  Tyr Pro Lys
            1010                1015                1020

Tyr Asn  Ser Phe Arg Glu Arg  Lys Ser Ala Thr Glu  Lys Val Tyr
            1025                1030                1035

Phe Tyr  Ser Asn Ile Met Asn  Ile Phe Lys Lys Ser  Ile Ser Leu
            1040                1045                1050

Ala Asp  Gly Arg Val Ile Glu  Arg Pro Leu Ile Glu  Val Asn Glu
            1055                1060                1065
```

-continued

| | | | | | | | | | | | |
|---|---|---|---|---|---|---|---|---|---|---|---|
|Glu|Thr|Gly|Glu|Ser|Val|Trp|Asn|Lys|Glu|Ser|Asp|Leu|Ala|Thr|
| |1070| | | |1075| | | |1080| | | | | |

Val Arg Arg Val Leu Ser Tyr Pro Gln Val Asn Val Val Lys Lys
   1085                   1090                 1095

Val Glu Val Gln Ser Gly Gly Phe Ser Lys Glu Leu Val Gln Pro
   1100                   1105                 1110

His Gly Asn Ser Asp Lys Leu Ile Pro Arg Lys Thr Lys Lys Met
   1115                   1120                 1125

Ile Trp Asp Thr Lys Lys Tyr Gly Gly Phe Asp Ser Pro Ile Val
   1130                   1135                 1140

Ala Tyr Ser Val Leu Val Met Ala Glu Arg Glu Lys Gly Lys Ser
   1145                   1150                 1155

Lys Lys Leu Lys Pro Val Lys Glu Leu Val Arg Ile Thr Ile Met
   1160                   1165                 1170

Glu Lys Glu Ser Phe Lys Glu Asn Thr Ile Asp Phe Leu Glu Arg
   1175                   1180                 1185

Arg Gly Leu Arg Asn Ile Gln Asp Glu Asn Ile Ile Leu Leu Pro
   1190                   1195                 1200

Lys Phe Ser Leu Phe Glu Leu Glu Asn Gly Arg Arg Arg Leu Leu
   1205                   1210                 1215

Ala Ser Ala Lys Glu Leu Gln Lys Gly Asn Glu Phe Ile Leu Pro
   1220                   1225                 1230

Asn Lys Leu Val Lys Leu Leu Tyr His Ala Lys Asn Ile His Asn
   1235                   1240                 1245

Thr Leu Glu Pro Glu His Leu Glu Tyr Val Glu Ser His Arg Ala
   1250                   1255                 1260

Asp Phe Gly Lys Ile Leu Asp Val Val Ser Val Phe Ser Glu Lys
   1265                   1270                 1275

Tyr Ile Leu Ala Glu Ala Lys Leu Glu Lys Ile Lys Glu Ile Tyr
   1280                   1285                 1290

Arg Lys Asn Met Asn Thr Glu Ile His Glu Met Ala Thr Ala Phe
   1295                   1300                 1305

Ile Asn Leu Leu Thr Phe Thr Ser Ile Gly Ala Pro Ala Thr Phe
   1310                   1315                 1320

Lys Phe Phe Gly His Asn Ile Glu Arg Lys Arg Tyr Ser Ser Val
   1325                   1330                 1335

Ala Glu Ile Leu Asn Ala Thr Leu Ile His Gln Ser Val Thr Gly
   1340                   1345                 1350

Leu Tyr Glu Thr Arg Ile Asp Leu Gly Lys Leu Gly Glu Asp
   1355                   1360                 1365

<210> SEQ ID NO 2
<211> LENGTH: 1375
<212> TYPE: PRT
<213> ORGANISM: Streptococcus acidominimus

<400> SEQUENCE: 2

Met Lys Lys Pro Tyr Ser Ile Gly Leu Asp Ile Gly Thr Asn Ser Val
1                5                   10                15

Gly Trp Ala Val Ile Thr Asp Asp Tyr Lys Val Pro Ala Lys Lys Met
                20                 25                30

Lys Val Leu Gly Asn Thr Asp Lys Lys Tyr Ile Lys Lys Asn Leu Leu
            35                 40                45

Gly Ala Leu Leu Phe Asp Ser Gly Glu Thr Ala Glu Val Thr Arg Leu
50               55                60

```
Lys Arg Thr Ala Arg Arg Tyr Thr Arg Lys Asn Arg Leu Arg
65                  70                  75                  80

Tyr Leu Gln Glu Ile Phe Ala Lys Glu Met Thr Lys Val Asp Glu Ser
            85                  90                  95

Phe Phe Gln Arg Leu Glu Glu Ser Phe Leu Thr Asp Asp Lys Thr
            100                 105                 110

Phe Asp Ser His Pro Ile Phe Gly Asn Lys Ala Glu Glu Asp Ala Tyr
            115                 120                 125

His Gln Lys Phe Pro Thr Ile Tyr His Leu Arg Lys Tyr Leu Ala Asp
            130                 135                 140

Ser Gln Glu Lys Ala Asp Leu Arg Leu Val Tyr Leu Ala Leu Ala His
145                 150                 155                 160

Met Ile Lys Tyr Arg Gly His Phe Leu Ile Glu Gly Glu Leu Asn Ala
            165                 170                 175

Glu Asn Thr Asp Val Gln Lys Leu Phe Asn Val Phe Val Glu Thr Tyr
            180                 185                 190

Asp Lys Ile Val Asp Glu Ser His Leu Ser Glu Ile Glu Val Asp Ala
            195                 200                 205

Ser Ser Ile Leu Thr Glu Lys Val Ser Lys Ser Arg Arg Leu Glu Asn
210                 215                 220

Leu Ile Lys Gln Tyr Pro Thr Glu Lys Lys Asn Thr Leu Phe Gly Asn
225                 230                 235                 240

Leu Ile Ala Leu Ala Leu Gly Leu Gln Pro Asn Phe Lys Thr Asn Phe
            245                 250                 255

Lys Leu Ser Glu Asp Ala Lys Leu Gln Phe Ser Lys Asp Thr Tyr Glu
            260                 265                 270

Glu Asp Leu Glu Glu Leu Leu Gly Lys Val Gly Asp Asp Tyr Ala Asp
            275                 280                 285

Leu Phe Ile Ser Ala Lys Asn Leu Tyr Asp Ala Ile Leu Leu Ser Gly
            290                 295                 300

Ile Leu Thr Val Asp Asp Asn Ser Thr Lys Ala Pro Leu Ser Ala Ser
305                 310                 315                 320

Met Ile Lys Arg Tyr Val Glu His His Glu Asp Leu Glu Lys Leu Lys
            325                 330                 335

Glu Phe Ile Lys Ile Asn Lys Leu Lys Leu Tyr His Asp Ile Phe Lys
            340                 345                 350

Asp Lys Thr Lys Asn Gly Tyr Ala Gly Tyr Ile Asp Asn Gly Val Lys
            355                 360                 365

Gln Asp Glu Phe Tyr Lys Tyr Leu Lys Thr Ile Leu Thr Lys Ile Asp
            370                 375                 380

Asp Ser Asp Tyr Phe Leu Asp Lys Ile Glu Arg Asp Asp Phe Leu Arg
385                 390                 395                 400

Lys Gln Arg Thr Phe Asp Asn Gly Ser Ile Pro His Gln Ile His Leu
            405                 410                 415

Gln Glu Met His Ser Ile Leu Arg Arg Gln Gly Glu Tyr Tyr Pro Phe
            420                 425                 430

Leu Lys Glu Asn Gln Ala Lys Ile Glu Lys Ile Leu Thr Phe Arg Ile
            435                 440                 445

Pro Tyr Tyr Val Gly Pro Leu Ala Arg Lys Asp Ser Arg Phe Ala Trp
            450                 455                 460

Ala Asn Tyr His Ser Asp Glu Pro Ile Thr Pro Trp Asn Phe Asp Glu
465                 470                 475                 480
```

```
Val Val Asp Lys Glu Lys Ser Ala Glu Lys Phe Ile Thr Arg Met Thr
            485                 490                 495

Leu Asn Asp Leu Tyr Leu Pro Glu Glu Lys Val Leu Pro Lys His Ser
        500                 505                 510

His Val Tyr Glu Thr Phe Thr Val Tyr Asn Glu Leu Thr Lys Ile Lys
        515                 520                 525

Tyr Val Asn Glu Gln Gly Glu Ser Phe Phe Asp Ala Asn Met Lys
        530                 535                 540

Gln Glu Ile Phe Asp His Val Phe Lys Glu Asn Arg Lys Val Thr Lys
545                 550                 555                 560

Ala Lys Leu Leu Ser Tyr Leu Asn Asn Glu Phe Glu Glu Phe Arg Ile
                565                 570                 575

Asn Asp Leu Ile Gly Leu Asp Lys Asp Ser Lys Ser Phe Asn Ala Ser
            580                 585                 590

Leu Gly Thr Tyr His Asp Leu Lys Lys Ile Leu Asp Lys Ser Phe Leu
        595                 600                 605

Asp Asp Lys Thr Asn Glu Gln Ile Ile Glu Asp Ile Val Leu Thr Leu
        610                 615                 620

Thr Leu Phe Glu Asp Arg Asp Met Ile His Glu Arg Leu Gln Lys Tyr
625                 630                 635                 640

Ser Asp Phe Phe Thr Ser Gln Gln Leu Lys Lys Leu Glu Arg Arg His
                645                 650                 655

Tyr Thr Gly Trp Gly Arg Leu Ser Lys Leu Ile Asn Gly Ile Arg
            660                 665                 670

Asn Lys Glu Asn Asn Lys Thr Ile Leu Asp Phe Leu Ile Asp Asp Gly
        675                 680                 685

His Ala Asn Arg Asn Phe Met Gln Leu Ile Asn Asp Glu Ser Leu Ser
        690                 695                 700

Phe Lys Thr Ile Ile Gln Glu Ala Gln Val Val Gly Asp Val Asp Asp
705                 710                 715                 720

Ile Glu Ala Val Val His Asp Leu Pro Gly Ser Pro Ala Ile Lys Lys
                725                 730                 735

Gly Ile Leu Gln Ser Val Lys Ile Val Asp Glu Leu Val Lys Val Met
            740                 745                 750

Gly Asp Asn Pro Asp Asn Ile Val Ile Glu Met Ala Arg Glu Asn Gln
        755                 760                 765

Thr Thr Gly Tyr Gly Arg Asn Lys Ser Asn Gln Arg Leu Lys Arg Leu
        770                 775                 780

Gln Asp Ser Leu Lys Glu Phe Gly Ser Asp Ile Leu Ser Lys Lys Lys
785                 790                 795                 800

Pro Ser Tyr Val Asp Ser Lys Val Glu Asn Ser His Leu Gln Asn Asp
                805                 810                 815

Arg Leu Phe Leu Tyr Tyr Ile Gln Asn Gly Lys Asp Met Tyr Thr Gly
            820                 825                 830

Glu Glu Leu Asp Ile Asp Arg Leu Ser Asp Tyr Asp Ile Asp His Ile
        835                 840                 845

Ile Pro Gln Ala Phe Ile Lys Asp Asn Ser Ile Asp Asn Lys Val Leu
        850                 855                 860

Thr Ser Ser Ala Lys Asn Arg Gly Lys Ser Asp Asp Val Pro Ser Ile
865                 870                 875                 880

Glu Ile Val Arg Asn Arg Arg Ser Tyr Trp Tyr Lys Leu Tyr Lys Ser
                885                 890                 895

Gly Leu Ile Ser Lys Arg Lys Phe Asp Asn Leu Thr Lys Ala Glu Arg
```

```
                900             905             910
Gly Gly Leu Thr Glu Ala Asp Lys Ala Gly Phe Ile Lys Arg Gln Leu
        915             920             925
Val Glu Thr Arg Gln Ile Thr Lys His Val Ala Gln Ile Leu Asp Ala
    930             935             940
Arg Phe Asn Thr Lys Arg Asp Glu Asn Asp Lys Val Ile Arg Asp Val
945             950             955             960
Lys Val Ile Thr Leu Lys Ser Asn Leu Val Ser Gln Phe Arg Lys Glu
            965             970             975
Phe Lys Phe Tyr Lys Val Arg Glu Ile Asn Asp Tyr His His Ala His
        980             985             990
Asp Ala Tyr Leu Asn Ala Val Val Gly Thr Ala Leu Leu Lys Lys Tyr
    995             1000            1005
Pro Lys Leu Thr Pro Glu Phe Val Tyr Gly Glu Tyr Lys Lys Tyr
    1010            1015            1020
Asp Val Arg Lys Leu Ile Ala Lys Ser Ser Asp Tyr Ser Glu
    1025            1030            1035
Met Gly Lys Ala Thr Ala Lys Tyr Phe Phe Tyr Ser Asn Leu Met
    1040            1045            1050
Asn Phe Phe Lys Thr Glu Val Lys Tyr Ala Asp Gly Arg Val Phe
    1055            1060            1065
Glu Arg Pro Asp Ile Glu Thr Asn Ala Asp Gly Glu Val Val Trp
    1070            1075            1080
Asn Lys Gln Lys Asp Phe Asp Ile Val Arg Lys Val Leu Ser Tyr
    1085            1090            1095
Pro Gln Val Asn Ile Val Lys Lys Val Glu Ala Gln Thr Gly Gly
    1100            1105            1110
Phe Ser Lys Glu Ser Ile Leu Ser Lys Gly Asp Ser Asp Lys Leu
    1115            1120            1125
Ile Pro Arg Lys Thr Lys Val Tyr Trp Asn Thr Lys Lys Tyr
    1130            1135            1140
Gly Gly Phe Asp Ser Pro Thr Val Ala Tyr Ser Val Leu Val Val
    1145            1150            1155
Ala Asp Ile Glu Lys Gly Lys Ala Lys Lys Leu Lys Thr Val Lys
    1160            1165            1170
Glu Leu Val Gly Ile Ser Ile Met Glu Arg Ser Phe Phe Glu Glu
    1175            1180            1185
Asn Pro Val Ser Phe Leu Glu Lys Lys Gly Tyr His Asn Val Gln
    1190            1195            1200
Glu Asp Lys Leu Ile Lys Leu Pro Lys Tyr Ser Leu Phe Glu Phe
    1205            1210            1215
Glu Gly Gly Arg Arg Leu Leu Ala Ser Ala Thr Glu Leu Gln
    1220            1225            1230
Lys Gly Asn Glu Val Met Leu Pro Ala His Leu Val Glu Leu Leu
    1235            1240            1245
Tyr His Ala His Arg Ile Asp Ser Phe Asn Ser Thr Glu His Leu
    1250            1255            1260
Lys Tyr Val Ser Glu His Lys Lys Glu Phe Glu Lys Val Leu Ser
    1265            1270            1275
Cys Val Glu Asn Phe Ser Asn Leu Tyr Val Asp Val Glu Lys Asn
    1280            1285            1290
Leu Ser Lys Val Arg Ala Ala Ala Glu Ser Met Thr Asn Phe Ser
    1295            1300            1305
```

-continued

Leu Glu Glu Ile Ser Ala Ser Phe Ile Asn Leu Leu Thr Leu Thr
1310                1315                1320

Ala Leu Gly Ala Pro Ala Asp Phe Asn Phe Leu Gly Glu Lys Ile
    1325                1330                1335

Pro Arg Lys Arg Tyr Thr Ser Thr Lys Glu Cys Leu Ser Ala Thr
    1340                1345                1350

Leu Ile His Gln Ser Val Thr Gly Leu Tyr Glu Thr Arg Ile Asp
    1355                1360                1365

Leu Ser Lys Leu Gly Glu Glu
    1370                1375

<210> SEQ ID NO 3
<211> LENGTH: 1367
<212> TYPE: PRT
<213> ORGANISM: Artificial Sequence
<220> FEATURE:
<223> OTHER INFORMATION: ENGINEERED NICKASE

<400> SEQUENCE: 3

Met Thr Lys Pro Tyr Ser Ile Gly Leu Asp Ile Gly Thr Asn Ser
1               5                   10                  15

Gly Trp Ala Val Ile Thr Asp Asp Tyr Lys Val Pro Ser Lys Lys Met
                20                  25                  30

Lys Val Leu Gly Asn Thr Ser Lys Lys Tyr Ile Lys Lys Asn Leu Leu
                35                  40                  45

Gly Ala Leu Leu Phe Asp Ser Gly Ile Thr Ala Glu Gly Arg Arg Leu
            50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                    85                  90                  95

Phe Phe Gln Arg Leu Asp Asp Ser Phe Leu Val Pro Asp Asp Lys Arg
                100                 105                 110

Asp Ser Lys Tyr Pro Ile Phe Gly Asn Leu Val Glu Glu Lys Ala Tyr
                115                 120                 125

His Asp Glu Phe Pro Thr Ile Tyr His Leu Arg Lys Tyr Leu Ala Asp
            130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
                180                 185                 190

Asn Ala Ile Phe Glu Ser Asp Leu Ser Leu Glu Asn Ser Lys Gln Leu
                195                 200                 205

Glu Glu Ile Val Lys Asp Lys Ile Ser Lys Leu Glu Lys Lys Asp Arg
            210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Lys Lys Tyr Phe
                245                 250                 255

Asn Leu Asp Glu Lys Ala Ser Leu His Phe Ser Lys Glu Ser Tyr Asp
                260                 265                 270

Glu Asp Leu Glu Thr Leu Leu Gly Tyr Ile Gly Asp Asp Tyr Ser Asp
            275                 280                 285

-continued

```
Val Phe Leu Lys Ala Lys Lys Leu Tyr Asp Ala Ile Leu Leu Ser Gly
    290                 295                 300

Ile Leu Thr Val Thr Asp Asn Gly Thr Glu Thr Pro Leu Ser Ser Ala
305                 310                 315                 320

Met Ile Met Arg Tyr Lys Glu His Glu Glu Asp Leu Gly Leu Leu Lys
                325                 330                 335

Ala Tyr Ile Arg Asn Ile Ser Leu Lys Thr Tyr Asn Glu Val Phe Asn
                340                 345                 350

Asp Asp Thr Lys Asn Gly Tyr Ala Gly Tyr Ile Asp Gly Lys Thr Asn
            355                 360                 365

Gln Glu Asp Phe Tyr Val Tyr Leu Lys Lys Leu Leu Ala Lys Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
                420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
                500                 505                 510

Leu Leu Tyr Glu Thr Phe Thr Val Tyr Asn Glu Leu Thr Lys Val Arg
            515                 520                 525

Phe Ile Ala Glu Gly Met Ser Asp Tyr Gln Phe Leu Asp Ser Lys Gln
    530                 535                 540

Lys Lys Asp Ile Val Arg Leu Tyr Phe Lys Gly Lys Arg Lys Val Lys
545                 550                 555                 560

Val Thr Asp Lys Asp Ile Ile Glu Tyr Leu His Ala Ile Asp Gly Tyr
                565                 570                 575

Asp Gly Ile Glu Leu Lys Gly Ile Glu Lys Gln Phe Asn Ser Ser Leu
            580                 585                 590

Ser Thr Tyr His Asp Leu Leu Asn Ile Ile Asn Asp Lys Glu Phe Leu
    595                 600                 605

Asp Asp Ser Ser Asn Glu Ala Ile Ile Glu Glu Ile Ile His Thr Leu
610                 615                 620

Thr Ile Phe Glu Asp Arg Glu Met Ile Lys Gln Arg Leu Ser Lys Phe
625                 630                 635                 640

Glu Asn Ile Phe Asp Lys Ser Val Leu Lys Lys Leu Ser Arg Arg His
                645                 650                 655

Tyr Thr Gly Trp Gly Lys Leu Ser Ala Lys Leu Ile Asn Gly Ile Arg
                660                 665                 670

Asp Glu Lys Ser Gly Asn Thr Ile Leu Asp Tyr Leu Ile Asp Asp Gly
            675                 680                 685

Ile Ser Asn Arg Asn Phe Met Gln Leu Ile His Asp Asp Ala Leu Ser
    690                 695                 700
```

-continued

```
Phe Lys Lys Lys Ile Gln Lys Ala Gln Ile Ile Gly Asp Lys Asp Lys
705                 710                 715                 720

Asp Asn Ile Lys Glu Val Val Lys Ser Leu Pro Gly Ser Pro Ala Ile
            725                 730                 735

Lys Lys Gly Ile Leu Gln Ser Ile Lys Ile Val Asp Glu Leu Val Lys
                740                 745                 750

Val Met Gly Arg Lys Pro Glu Ser Ile Val Val Glu Met Ala Arg Glu
            755                 760                 765

Asn Gln Tyr Thr Asn Gln Gly Lys Ser Asn Ser Gln Gln Arg Leu Lys
770                 775                 780

Arg Leu Glu Glu Ser Leu Glu Glu Leu Gly Ser Lys Ile Leu Lys Glu
785                 790                 795                 800

Asn Ile Pro Ala Lys Leu Ser Lys Ile Asp Asn Asn Ser Leu Gln Asn
                805                 810                 815

Asp Arg Leu Tyr Leu Tyr Tyr Leu Gln Asn Gly Lys Asp Met Tyr Thr
            820                 825                 830

Gly Asp Asp Leu Asp Ile Asp Arg Leu Ser Asn Tyr Asp Ile Asp Ala
            835                 840                 845

Ile Ile Pro Gln Ala Phe Leu Lys Asp Asn Ser Ile Asp Asn Lys Val
850                 855                 860

Leu Val Ser Ser Ala Ser Asn Arg Gly Lys Ser Asp Asp Val Pro Ser
865                 870                 875                 880

Leu Glu Val Val Lys Lys Arg Lys Thr Leu Trp Tyr Gln Leu Leu Lys
                885                 890                 895

Ser Lys Leu Ile Ser Gln Arg Lys Phe Asp Asn Leu Thr Lys Ala Glu
            900                 905                 910

Arg Gly Gly Leu Ser Pro Glu Asp Lys Ala Gly Phe Ile Gln Arg Gln
            915                 920                 925

Leu Val Glu Thr Arg Gln Ile Thr Lys His Val Ala Arg Leu Leu Asp
930                 935                 940

Glu Lys Phe Asn Asn Lys Lys Asp Glu Asn Asn Arg Ala Val Arg Thr
945                 950                 955                 960

Val Lys Ile Ile Thr Leu Lys Ser Thr Leu Val Ser Gln Phe Arg Lys
                965                 970                 975

Asp Phe Glu Leu Tyr Lys Val Arg Glu Ile Asn Asp Phe His His Ala
            980                 985                 990

His Asp Ala Tyr Leu Asn Ala Val  Val Ala Ser Ala Leu  Leu Lys Lys
            995                 1000                1005

Tyr Pro Lys Leu Glu Pro Glu  Phe Val Tyr Gly Asp   Tyr Pro Lys
    1010                1015                1020

Tyr Asn  Ser Phe Arg Glu Arg  Lys Ser Ala Thr Glu   Lys Val Tyr
    1025                1030                1035

Phe Tyr Ser Asn Ile Met Asn  Ile Phe Lys Lys Ser   Ile Ser Leu
    1040                1045                1050

Ala Asp  Gly Arg Val Ile Glu  Arg Pro Leu Ile Glu   Val Asn Glu
    1055                1060                1065

Glu Thr  Gly Glu Ser Val Trp  Asn Lys Glu Ser Asp   Leu Ala Thr
    1070                1075                1080

Val Arg  Arg Val Leu Ser Tyr  Pro Gln Val Asn Val   Val Lys Lys
    1085                1090                1095

Val Glu  Val Gln Ser Gly Gly  Phe Ser Lys Glu Leu   Val Gln Pro
    1100                1105                1110

His Gly  Asn Ser Asp Lys Leu  Ile Pro Arg Lys Thr   Lys Lys Met
```

```
                    1115                1120                1125

Ile Trp Asp Thr Lys Lys Tyr Gly Gly Phe Asp Ser Pro Ile Val
            1130                1135                1140

Ala Tyr Ser Val Leu Val Met Ala Glu Arg Glu Lys Gly Lys Ser
            1145                1150                1155

Lys Lys Leu Lys Pro Val Lys Glu Leu Val Arg Ile Thr Ile Met
            1160                1165                1170

Glu Lys Glu Ser Phe Lys Glu Asn Thr Ile Asp Phe Leu Glu Arg
            1175                1180                1185

Arg Gly Leu Arg Asn Ile Gln Asp Glu Asn Ile Ile Leu Leu Pro
            1190                1195                1200

Lys Phe Ser Leu Phe Glu Leu Glu Asn Gly Arg Arg Arg Leu Leu
            1205                1210                1215

Ala Ser Ala Lys Glu Leu Gln Lys Gly Asn Glu Phe Ile Leu Pro
            1220                1225                1230

Asn Lys Leu Val Lys Leu Leu Tyr His Ala Lys Asn Ile His Asn
            1235                1240                1245

Thr Leu Glu Pro Glu His Leu Glu Tyr Val Glu Ser His Arg Ala
            1250                1255                1260

Asp Phe Gly Lys Ile Leu Asp Val Val Ser Val Phe Ser Glu Lys
            1265                1270                1275

Tyr Ile Leu Ala Glu Ala Lys Leu Glu Lys Ile Lys Glu Ile Tyr
            1280                1285                1290

Arg Lys Asn Met Asn Thr Glu Ile His Glu Met Ala Thr Ala Phe
            1295                1300                1305

Ile Asn Leu Leu Thr Phe Thr Ser Ile Gly Ala Pro Ala Thr Phe
            1310                1315                1320

Lys Phe Phe Gly His Asn Ile Glu Arg Lys Arg Tyr Ser Ser Val
            1325                1330                1335

Ala Glu Ile Leu Asn Ala Thr Leu Ile His Gln Ser Val Thr Gly
            1340                1345                1350

Leu Tyr Glu Thr Arg Ile Asp Leu Gly Lys Leu Gly Glu Asp
            1355                1360                1365

<210> SEQ ID NO 4
<211> LENGTH: 1367
<212> TYPE: PRT
<213> ORGANISM: Artificial Sequence
<220> FEATURE:
<223> OTHER INFORMATION: ENGINEERED NICKASE

<400> SEQUENCE: 4

Met Thr Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Ala Leu Leu Phe Asp Ser Gly Ile Thr Ala Glu Gly Arg Arg Leu
    50                  55                  60

Lys Arg Thr Ala Arg Arg Arg Tyr Thr Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
```

-continued

```
                100                 105                 110
Asp Ser Lys Tyr Pro Ile Phe Gly Asn Leu Val Glu Glu Lys Ala Tyr
            115                 120                 125
His Asp Glu Phe Pro Thr Ile Tyr His Leu Arg Lys Tyr Leu Ala Asp
        130                 135                 140
Ser Thr Lys Lys Ala Asp Leu Arg Leu Val Tyr Leu Ala Leu Ala His
145                 150                 155                 160
Met Ile Lys Tyr Arg Gly His Phe Leu Ile Glu Gly Glu Phe Asn Ser
                165                 170                 175
Lys Asn Asn Asp Ile Gln Lys Asn Phe Gln Asp Phe Leu Asp Thr Tyr
            180                 185                 190
Asn Ala Ile Phe Glu Ser Asp Leu Ser Leu Glu Asn Ser Lys Gln Leu
        195                 200                 205
Glu Glu Ile Val Lys Asp Lys Ile Ser Lys Leu Glu Lys Lys Asp Arg
210                 215                 220
Ile Leu Lys Leu Phe Pro Gly Glu Lys Asn Ser Gly Ile Phe Ser Glu
225                 230                 235                 240
Phe Leu Lys Leu Ile Val Gly Asn Gln Ala Asp Phe Lys Lys Tyr Phe
                245                 250                 255
Asn Leu Asp Glu Lys Ala Ser Leu His Phe Ser Lys Glu Ser Tyr Asp
            260                 265                 270
Glu Asp Leu Glu Thr Leu Leu Gly Tyr Ile Gly Asp Asp Tyr Ser Asp
        275                 280                 285
Val Phe Leu Lys Ala Lys Lys Leu Tyr Asp Ala Ile Leu Leu Ser Gly
    290                 295                 300
Ile Leu Thr Val Thr Asp Asn Gly Thr Glu Thr Pro Leu Ser Ser Ala
305                 310                 315                 320
Met Ile Met Arg Tyr Lys Glu His Glu Glu Asp Leu Gly Leu Leu Lys
                325                 330                 335
Ala Tyr Ile Arg Asn Ile Ser Leu Lys Thr Tyr Asn Glu Val Phe Asn
            340                 345                 350
Asp Asp Thr Lys Asn Gly Tyr Ala Gly Tyr Ile Asp Gly Lys Thr Asn
        355                 360                 365
Gln Glu Asp Phe Tyr Val Tyr Leu Lys Lys Leu Leu Ala Lys Phe Glu
    370                 375                 380
Gly Ala Asp Tyr Phe Leu Glu Lys Ile Asp Arg Glu Asp Phe Leu Arg
385                 390                 395                 400
Lys Gln Arg Thr Phe Asp Asn Gly Ser Ile Pro Tyr Gln Ile His Leu
                405                 410                 415
Gln Glu Met Arg Ala Ile Leu Asp Lys Gln Ala Lys Phe Tyr Pro Phe
            420                 425                 430
Leu Ala Lys Asn Lys Glu Arg Ile Glu Lys Ile Leu Thr Phe Arg Ile
        435                 440                 445
Pro Tyr Tyr Val Gly Pro Leu Ala Arg Gly Asn Ser Asp Phe Ala Trp
    450                 455                 460
Ser Ile Arg Lys Arg Asn Glu Lys Ile Thr Pro Trp Asn Phe Glu Asp
465                 470                 475                 480
Val Ile Asp Lys Glu Ser Ser Ala Glu Ala Phe Ile Asn Arg Met Thr
                485                 490                 495
Ser Phe Asp Leu Tyr Leu Pro Glu Glu Lys Val Leu Pro Lys His Ser
            500                 505                 510
Leu Leu Tyr Glu Thr Phe Thr Val Tyr Asn Glu Leu Thr Lys Val Arg
        515                 520                 525
```

```
Phe Ile Ala Glu Gly Met Ser Asp Tyr Gln Phe Leu Asp Ser Lys Gln
            530                 535                 540
Lys Lys Asp Ile Val Arg Leu Tyr Phe Lys Gly Lys Arg Lys Val Lys
545                 550                 555                 560
Val Thr Asp Lys Asp Ile Ile Glu Tyr Leu His Ala Ile Asp Gly Tyr
                565                 570                 575
Asp Gly Ile Glu Leu Lys Gly Ile Glu Lys Gln Phe Asn Ser Ser Leu
                580                 585                 590
Ser Thr Tyr His Asp Leu Leu Asn Ile Ile Asn Asp Lys Glu Phe Leu
            595                 600                 605
Asp Asp Ser Ser Asn Glu Ala Ile Ile Glu Ile Ile His Thr Leu
610                 615                 620
Thr Ile Phe Glu Asp Arg Glu Met Ile Lys Gln Arg Leu Ser Lys Phe
625                 630                 635                 640
Glu Asn Ile Phe Asp Lys Ser Val Leu Lys Lys Leu Ser Arg Arg His
                645                 650                 655
Tyr Thr Gly Trp Gly Lys Leu Ser Ala Lys Leu Ile Asn Gly Ile Arg
                660                 665                 670
Asp Glu Lys Ser Gly Asn Thr Ile Leu Asp Tyr Leu Ile Asp Asp Gly
            675                 680                 685
Ile Ser Asn Arg Asn Phe Met Gln Leu Ile His Asp Asp Ala Leu Ser
            690                 695                 700
Phe Lys Lys Lys Ile Gln Lys Ala Gln Ile Ile Gly Asp Lys Asp Lys
705                 710                 715                 720
Asp Asn Ile Lys Glu Val Val Lys Ser Leu Pro Gly Ser Pro Ala Ile
                725                 730                 735
Lys Lys Gly Ile Leu Gln Ser Ile Lys Ile Val Asp Glu Leu Val Lys
            740                 745                 750
Val Met Gly Arg Lys Pro Glu Ser Ile Val Val Glu Met Ala Arg Glu
            755                 760                 765
Asn Gln Tyr Thr Asn Gln Gly Lys Ser Asn Ser Gln Gln Arg Leu Lys
770                 775                 780
Arg Leu Glu Glu Ser Leu Glu Glu Leu Gly Ser Lys Ile Leu Lys Glu
785                 790                 795                 800
Asn Ile Pro Ala Lys Leu Ser Lys Ile Asp Asn Asn Ser Leu Gln Asn
                805                 810                 815
Asp Arg Leu Tyr Leu Tyr Tyr Leu Gln Asn Gly Lys Asp Met Tyr Thr
                820                 825                 830
Gly Asp Asp Leu Asp Ile Asp Arg Leu Ser Asn Tyr Asp Ile Asp His
            835                 840                 845
Ile Ile Pro Gln Ala Phe Leu Lys Asp Asn Ser Ile Asp Asn Lys Val
850                 855                 860
Leu Val Ser Ser Ala Ser Ala Arg Gly Lys Ser Asp Asp Val Pro Ser
865                 870                 875                 880
Leu Glu Val Val Lys Lys Arg Lys Thr Leu Trp Tyr Gln Leu Leu Lys
                885                 890                 895
Ser Lys Leu Ile Ser Gln Arg Lys Phe Asp Asn Leu Thr Lys Ala Glu
            900                 905                 910
Arg Gly Gly Leu Ser Pro Glu Asp Lys Ala Gly Phe Ile Gln Arg Gln
            915                 920                 925
Leu Val Glu Thr Arg Gln Ile Thr Lys His Val Ala Arg Leu Leu Asp
930                 935                 940
```

-continued

```
Glu Lys Phe Asn Asn Lys Lys Asp Glu Asn Asn Arg Ala Val Arg Thr
945                 950                 955                 960

Val Lys Ile Ile Thr Leu Lys Ser Thr Leu Val Ser Gln Phe Arg Lys
            965                 970                 975

Asp Phe Glu Leu Tyr Lys Val Arg Glu Ile Asn Asp Phe His His Ala
                980                 985                 990

His Asp Ala Tyr Leu Asn Ala Val  Val Ala Ser Ala Leu  Leu Lys Lys
            995                 1000                 1005

Tyr Pro  Lys Leu Glu Pro  Phe Val Tyr Gly Asp  Tyr Pro Lys
    1010                 1015                 1020

Tyr Asn  Ser Phe Arg Glu  Arg Lys Ser Ala Thr  Glu  Lys Val Tyr
    1025                 1030                 1035

Phe Tyr  Ser Asn Ile Met  Asn Ile Phe Lys Lys Ser  Ile Ser Leu
    1040                 1045                 1050

Ala Asp  Gly Arg Val Ile  Glu Arg Pro Leu Ile Glu  Val Asn Glu
    1055                 1060                 1065

Glu Thr  Gly Glu Ser Val  Trp Asn Lys Glu Ser Asp  Leu Ala Thr
    1070                 1075                 1080

Val Arg  Arg Val Leu Ser  Tyr Pro Gln Val Asn Val  Val Lys Lys
    1085                 1090                 1095

Val Glu  Val Gln Ser Gly  Gly  Phe Ser Lys Glu Leu  Val Gln Pro
    1100                 1105                 1110

His Gly  Asn Ser Asp Lys  Leu  Ile Pro Arg Lys Thr  Lys Lys Met
    1115                 1120                 1125

Ile Trp  Asp Thr Lys Lys  Tyr  Gly Gly Phe Asp Ser  Pro Ile Val
    1130                 1135                 1140

Ala Tyr  Ser Val Leu Val  Met  Ala Glu Arg Glu Lys  Gly Lys Ser
    1145                 1150                 1155

Lys Lys  Leu Lys Pro Val  Lys  Glu Leu Val Arg Ile  Thr Ile Met
    1160                 1165                 1170

Glu Lys  Glu Ser Phe Lys  Glu  Asn Thr Ile Asp Phe  Leu Glu Arg
    1175                 1180                 1185

Arg Gly  Leu Arg Asn Ile  Gln  Asp Glu Asn Ile Ile  Leu Leu Pro
    1190                 1195                 1200

Lys Phe  Ser Leu Phe Glu  Leu  Glu Asn Gly Arg Arg  Arg Leu Leu
    1205                 1210                 1215

Ala Ser  Ala Lys Glu Leu  Gln  Lys Gly Asn Glu Phe  Ile Leu Pro
    1220                 1225                 1230

Asn Lys  Leu Val Lys Leu  Leu  Tyr His Ala Lys Asn  Ile His Asn
    1235                 1240                 1245

Thr Leu  Glu Pro Glu His  Leu  Glu Tyr Val Glu Ser  His Arg Ala
    1250                 1255                 1260

Asp Phe  Gly Lys Ile Leu  Asp  Val Val Ser Val Phe  Ser Glu Lys
    1265                 1270                 1275

Tyr Ile  Leu Ala Glu Ala  Lys  Leu Glu Lys Ile Lys  Glu Ile Tyr
    1280                 1285                 1290

Arg Lys  Asn Met Asn Thr  Glu  Ile His Glu Met Ala  Thr Ala Phe
    1295                 1300                 1305

Ile Asn  Leu Leu Thr Phe  Thr  Ser Ile Gly Ala Pro  Ala Thr Phe
    1310                 1315                 1320

Lys Phe  Phe Gly His Asn  Ile  Glu Arg Lys Arg Tyr  Ser Ser Val
    1325                 1330                 1335

Ala Glu  Ile Leu Asn Ala Thr  Leu Ile His Gln Ser  Val Thr Gly
```

-continued

```
                1340                1345                1350
        Leu Tyr Glu Thr Arg Ile Asp Leu Gly Lys Leu Gly Glu Asp
            1355                1360                1365

<210> SEQ ID NO 5
<211> LENGTH: 1375
<212> TYPE: PRT
<213> ORGANISM: Artificial Sequence
<220> FEATURE:
<223> OTHER INFORMATION: ENGINEERED NICKASE

<400> SEQUENCE: 5

Met Lys Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ala Lys Lys Met
            20                  25                  30

Lys Val Leu Gly Asn Thr Asp Lys Lys Tyr Ile Lys Lys Asn Leu Leu
        35                  40                  45

Gly Ala Leu Leu Phe Asp Ser Gly Glu Thr Ala Glu Val Thr Arg Leu
    50                  55                  60

Lys Arg Thr Ala Arg Arg Arg Tyr Thr Arg Arg Lys Asn Arg Leu Arg
65                  70                  75                  80

Tyr Leu Gln Glu Ile Phe Ala Lys Glu Met Thr Lys Val Asp Glu Ser
                85                  90                  95

Phe Phe Gln Arg Leu Glu Glu Ser Phe Leu Thr Asp Asp Lys Thr
            100                 105                 110

Phe Asp Ser His Pro Ile Phe Gly Asn Lys Ala Glu Glu Asp Ala Tyr
        115                 120                 125

His Gln Lys Phe Pro Thr Ile Tyr His Leu Arg Lys Tyr Leu Ala Asp
    130                 135                 140

Ser Gln Glu Lys Ala Asp Leu Arg Leu Val Tyr Leu Ala Leu Ala His
145                 150                 155                 160

Met Ile Lys Tyr Arg Gly His Phe Leu Ile Glu Gly Glu Leu Asn Ala
                165                 170                 175

Glu Asn Thr Asp Val Gln Lys Leu Phe Asn Val Phe Val Glu Thr Tyr
            180                 185                 190

Asp Lys Ile Val Asp Glu Ser His Leu Ser Glu Ile Glu Val Asp Ala
        195                 200                 205

Ser Ser Ile Leu Thr Glu Lys Val Ser Lys Ser Arg Arg Leu Glu Asn
    210                 215                 220

Leu Ile Lys Gln Tyr Pro Thr Glu Lys Lys Asn Thr Leu Phe Gly Asn
225                 230                 235                 240

Leu Ile Ala Leu Ala Leu Gly Leu Gln Pro Asn Phe Lys Thr Asn Phe
                245                 250                 255

Lys Leu Ser Glu Asp Ala Lys Leu Gln Phe Ser Lys Asp Thr Tyr Glu
            260                 265                 270

Glu Asp Leu Glu Glu Leu Leu Gly Lys Val Gly Asp Asp Tyr Ala Asp
        275                 280                 285

Leu Phe Ile Ser Ala Lys Asn Leu Tyr Asp Ala Ile Leu Leu Ser Gly
    290                 295                 300

Ile Leu Thr Val Asp Asp Asn Ser Thr Lys Ala Pro Leu Ser Ala Ser
305                 310                 315                 320

Met Ile Lys Arg Tyr Val Glu His His Glu Asp Leu Glu Lys Leu Lys
                325                 330                 335

Glu Phe Ile Lys Ile Asn Lys Leu Lys Leu Tyr His Asp Ile Phe Lys
```

-continued

```
                340                 345                 350
Asp Lys Thr Lys Asn Gly Tyr Ala Gly Tyr Ile Asp Asn Gly Val Lys
                355                 360                 365
Gln Asp Glu Phe Tyr Lys Tyr Leu Lys Thr Ile Leu Thr Lys Ile Asp
            370                 375                 380
Asp Ser Asp Tyr Phe Leu Asp Lys Ile Glu Arg Asp Asp Phe Leu Arg
385                 390                 395                 400
Lys Gln Arg Thr Phe Asp Asn Gly Ser Ile Pro His Gln Ile His Leu
                405                 410                 415
Gln Glu Met His Ser Ile Leu Arg Arg Gln Gly Glu Tyr Tyr Pro Phe
            420                 425                 430
Leu Lys Glu Asn Gln Ala Lys Ile Glu Lys Ile Leu Thr Phe Arg Ile
        435                 440                 445
Pro Tyr Tyr Val Gly Pro Leu Ala Arg Lys Asp Ser Arg Phe Ala Trp
    450                 455                 460
Ala Asn Tyr His Ser Asp Glu Pro Ile Thr Pro Trp Asn Phe Asp Glu
465                 470                 475                 480
Val Val Asp Lys Glu Lys Ser Ala Glu Lys Phe Ile Thr Arg Met Thr
                485                 490                 495
Leu Asn Asp Leu Tyr Leu Pro Glu Glu Lys Val Leu Pro Lys His Ser
            500                 505                 510
His Val Tyr Glu Thr Phe Thr Val Tyr Asn Glu Leu Thr Lys Ile Lys
        515                 520                 525
Tyr Val Asn Glu Gln Gly Glu Ser Phe Phe Phe Asp Ala Asn Met Lys
    530                 535                 540
Gln Glu Ile Phe Asp His Val Phe Lys Glu Asn Arg Lys Val Thr Lys
545                 550                 555                 560
Ala Lys Leu Leu Ser Tyr Leu Asn Asn Glu Phe Glu Glu Phe Arg Ile
                565                 570                 575
Asn Asp Leu Ile Gly Leu Asp Lys Asp Ser Lys Ser Phe Asn Ala Ser
            580                 585                 590
Leu Gly Thr Tyr His Asp Leu Lys Lys Ile Leu Asp Lys Ser Phe Leu
        595                 600                 605
Asp Asp Lys Thr Asn Glu Gln Ile Ile Glu Asp Ile Val Leu Thr Leu
    610                 615                 620
Thr Leu Phe Glu Asp Arg Asp Met Ile His Glu Arg Leu Gln Lys Tyr
625                 630                 635                 640
Ser Asp Phe Phe Thr Ser Gln Gln Leu Lys Lys Leu Glu Arg Arg His
                645                 650                 655
Tyr Thr Gly Trp Gly Arg Leu Ser Tyr Lys Leu Ile Asn Gly Ile Arg
            660                 665                 670
Asn Lys Glu Asn Asn Lys Thr Ile Leu Asp Phe Leu Ile Asp Asp Gly
        675                 680                 685
His Ala Asn Arg Asn Phe Met Gln Leu Ile Asn Asp Glu Ser Leu Ser
    690                 695                 700
Phe Lys Thr Ile Ile Gln Glu Ala Gln Val Val Gly Asp Val Asp Asp
705                 710                 715                 720
Ile Glu Ala Val Val His Asp Leu Pro Gly Ser Pro Ala Ile Lys Lys
                725                 730                 735
Gly Ile Leu Gln Ser Val Lys Ile Val Asp Glu Leu Val Lys Val Met
            740                 745                 750
Gly Asp Asn Pro Asp Asn Ile Val Ile Glu Met Ala Arg Glu Asn Gln
        755                 760                 765
```

-continued

```
Thr Thr Gly Tyr Gly Arg Asn Lys Ser Asn Gln Arg Leu Lys Arg Leu
    770             775             780
Gln Asp Ser Leu Lys Glu Phe Gly Ser Asp Ile Leu Ser Lys Lys Lys
785             790             795             800
Pro Ser Tyr Val Asp Ser Lys Val Glu Asn Ser His Leu Gln Asn Asp
            805             810             815
Arg Leu Phe Leu Tyr Tyr Ile Gln Asn Gly Lys Asp Met Tyr Thr Gly
            820             825             830
Glu Glu Leu Asp Ile Asp Arg Leu Ser Asp Tyr Asp Ile Asp Ala Ile
        835             840             845
Ile Pro Gln Ala Phe Ile Lys Asp Asn Ser Ile Asp Asn Lys Val Leu
    850             855             860
Thr Ser Ser Ala Lys Asn Arg Gly Lys Ser Asp Asp Val Pro Ser Ile
865             870             875             880
Glu Ile Val Arg Asn Arg Arg Ser Tyr Trp Tyr Lys Leu Tyr Lys Ser
            885             890             895
Gly Leu Ile Ser Lys Arg Lys Phe Asp Asn Leu Thr Lys Ala Glu Arg
            900             905             910
Gly Gly Leu Thr Glu Ala Asp Lys Ala Gly Phe Ile Lys Arg Gln Leu
        915             920             925
Val Glu Thr Arg Gln Ile Thr Lys His Val Ala Gln Ile Leu Asp Ala
    930             935             940
Arg Phe Asn Thr Lys Arg Asp Glu Asn Asp Lys Val Ile Arg Asp Val
945             950             955             960
Lys Val Ile Thr Leu Lys Ser Asn Leu Val Ser Gln Phe Arg Lys Glu
            965             970             975
Phe Lys Phe Tyr Lys Val Arg Glu Ile Asn Asp Tyr His His Ala His
            980             985             990
Asp Ala Tyr Leu Asn Ala Val Val  Gly Thr Ala Leu  Leu Lys Lys Tyr
        995             1000            1005
Pro Lys  Leu Thr Pro Glu Phe  Val Tyr Gly Glu Tyr  Lys Lys Tyr
    1010            1015            1020
Asp Val  Arg Lys Leu Ile Ala  Lys Ser Glu Asp  Tyr Ser Glu
    1025            1030            1035
Met Gly  Lys Ala Thr Ala Lys  Tyr Phe Phe Tyr Ser  Asn Leu Met
    1040            1045            1050
Asn Phe  Phe Lys Thr Glu Val  Lys Tyr Ala Asp Gly  Arg Val Phe
    1055            1060            1065
Glu Arg  Pro Asp Ile Glu Thr  Asn Ala Asp Gly Glu  Val Val Trp
    1070            1075            1080
Asn Lys  Gln Lys Asp Phe Asp  Ile Val Arg Lys Val  Leu Ser Tyr
    1085            1090            1095
Pro Gln  Val Asn Ile Val Lys  Val Glu Ala Gln  Thr Gly Gly
    1100            1105            1110
Phe Ser  Lys Glu Ser Ile Leu  Ser Lys Gly Asp Ser  Asp Lys Leu
    1115            1120            1125
Ile Pro  Arg Lys Thr Lys Lys  Val Tyr Trp Asn Thr  Lys Lys Tyr
    1130            1135            1140
Gly Gly  Phe Asp Ser Pro Thr  Val Ala Tyr Ser Val  Leu Val Val
    1145            1150            1155
Ala Asp  Ile Glu Lys Gly Lys  Ala Lys Lys Leu Lys  Thr Val Lys
    1160            1165            1170
```

```
Glu Leu Val Gly Ile Ser Ile Met Glu Arg Ser Phe Phe Glu Glu
    1175                1180                1185

Asn Pro Val Ser Phe Leu Glu Lys Lys Gly Tyr His Asn Val Gln
    1190                1195                1200

Glu Asp Lys Leu Ile Lys Leu Pro Lys Tyr Ser Leu Phe Glu Phe
    1205                1210                1215

Glu Gly Gly Arg Arg Leu Leu Ala Ser Ala Thr Glu Leu Gln
    1220                1225                1230

Lys Gly Asn Glu Val Met Leu Pro Ala His Leu Val Glu Leu Leu
    1235                1240                1245

Tyr His Ala His Arg Ile Asp Ser Phe Asn Ser Thr Glu His Leu
    1250                1255                1260

Lys Tyr Val Ser Glu His Lys Lys Glu Phe Glu Lys Val Leu Ser
    1265                1270                1275

Cys Val Glu Asn Phe Ser Asn Leu Tyr Val Asp Val Glu Lys Asn
    1280                1285                1290

Leu Ser Lys Val Arg Ala Ala Ala Glu Ser Met Thr Asn Phe Ser
    1295                1300                1305

Leu Glu Glu Ile Ser Ala Ser Phe Ile Asn Leu Leu Thr Leu Thr
    1310                1315                1320

Ala Leu Gly Ala Pro Ala Asp Phe Asn Phe Leu Gly Glu Lys Ile
    1325                1330                1335

Pro Arg Lys Arg Tyr Thr Ser Thr Lys Glu Cys Leu Ser Ala Thr
    1340                1345                1350

Leu Ile His Gln Ser Val Thr Gly Leu Tyr Glu Thr Arg Ile Asp
    1355                1360                1365

Leu Ser Lys Leu Gly Glu Glu
    1370                1375

<210> SEQ ID NO 6
<211> LENGTH: 1375
<212> TYPE: PRT
<213> ORGANISM: Artificial Sequence
<220> FEATURE:
<223> OTHER INFORMATION: ENGINEERED NICKASE

<400> SEQUENCE: 6

Met Lys Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ala Lys Lys Met
            20                  25                  30

Lys Val Leu Gly Asn Thr Asp Lys Tyr Ile Lys Lys Asn Leu Leu
        35                  40                  45

Gly Ala Leu Leu Phe Asp Ser Gly Glu Thr Ala Glu Val Thr Arg Leu
    50                  55                  60

Lys Arg Thr Ala Arg Arg Arg Tyr Thr Arg Arg Lys Asn Arg Leu Arg
65                  70                  75                  80

Tyr Leu Gln Glu Ile Phe Ala Lys Glu Met Thr Lys Val Asp Glu Ser
                85                  90                  95

Phe Phe Gln Arg Leu Glu Glu Ser Phe Leu Thr Asp Asp Lys Thr
            100                 105                 110

Phe Asp Ser His Pro Ile Phe Gly Asn Lys Ala Glu Glu Asp Ala Tyr
        115                 120                 125

His Gln Lys Phe Pro Thr Ile Tyr His Leu Arg Lys Tyr Leu Ala Asp
    130                 135                 140
```

```
Ser Gln Glu Lys Ala Asp Leu Arg Leu Val Tyr Leu Ala Leu Ala His
145                 150                 155                 160

Met Ile Lys Tyr Arg Gly His Phe Leu Ile Glu Gly Glu Leu Asn Ala
            165                 170                 175

Glu Asn Thr Asp Val Gln Lys Leu Phe Asn Val Phe Val Glu Thr Tyr
            180                 185                 190

Asp Lys Ile Val Asp Glu Ser His Leu Ser Glu Ile Glu Val Asp Ala
            195                 200                 205

Ser Ser Ile Leu Thr Glu Lys Val Ser Lys Ser Arg Arg Leu Glu Asn
210                 215                 220

Leu Ile Lys Gln Tyr Pro Thr Glu Lys Asn Thr Leu Phe Gly Asn
225                 230                 235                 240

Leu Ile Ala Leu Ala Leu Gly Leu Gln Pro Asn Phe Lys Thr Asn Phe
            245                 250                 255

Lys Leu Ser Glu Asp Ala Lys Leu Gln Phe Ser Lys Asp Thr Tyr Glu
            260                 265                 270

Glu Asp Leu Glu Glu Leu Leu Gly Lys Val Gly Asp Asp Tyr Ala Asp
            275                 280                 285

Leu Phe Ile Ser Ala Lys Asn Leu Tyr Asp Ala Ile Leu Leu Ser Gly
            290                 295                 300

Ile Leu Thr Val Asp Asp Asn Ser Thr Lys Ala Pro Leu Ser Ala Ser
305                 310                 315                 320

Met Ile Lys Arg Tyr Val Glu His His Glu Asp Leu Glu Lys Leu Lys
            325                 330                 335

Glu Phe Ile Lys Ile Asn Lys Leu Lys Leu Tyr His Asp Ile Phe Lys
            340                 345                 350

Asp Lys Thr Lys Asn Gly Tyr Ala Gly Tyr Ile Asp Asn Gly Val Lys
            355                 360                 365

Gln Asp Glu Phe Tyr Lys Tyr Leu Lys Thr Ile Leu Thr Lys Ile Asp
            370                 375                 380

Asp Ser Asp Tyr Phe Leu Asp Lys Ile Glu Arg Asp Asp Phe Leu Arg
385                 390                 395                 400

Lys Gln Arg Thr Phe Asp Asn Gly Ser Ile Pro His Gln Ile His Leu
            405                 410                 415

Gln Glu Met His Ser Ile Leu Arg Arg Gln Gly Glu Tyr Tyr Pro Phe
            420                 425                 430

Leu Lys Glu Asn Gln Ala Lys Ile Glu Lys Ile Leu Thr Phe Arg Ile
            435                 440                 445

Pro Tyr Tyr Val Gly Pro Leu Ala Arg Lys Asp Ser Arg Phe Ala Trp
450                 455                 460

Ala Asn Tyr His Ser Asp Glu Pro Ile Thr Pro Trp Asn Phe Asp Glu
465                 470                 475                 480

Val Val Asp Lys Glu Lys Ser Ala Glu Lys Phe Ile Thr Arg Met Thr
            485                 490                 495

Leu Asn Asp Leu Tyr Leu Pro Glu Glu Lys Val Leu Pro Lys His Ser
            500                 505                 510

His Val Tyr Glu Thr Phe Thr Val Tyr Asn Glu Leu Thr Lys Ile Lys
            515                 520                 525

Tyr Val Asn Glu Gln Gly Glu Ser Phe Phe Asp Ala Asn Met Lys
            530                 535                 540

Gln Glu Ile Phe Asp His Val Phe Lys Glu Asn Arg Lys Val Thr Lys
545                 550                 555                 560

Ala Lys Leu Leu Ser Tyr Leu Asn Asn Glu Phe Glu Glu Phe Arg Ile
```

-continued

```
                565                 570                 575
Asn Asp Leu Ile Gly Leu Asp Lys Asp Ser Lys Ser Phe Asn Ala Ser
                580                 585                 590

Leu Gly Thr Tyr His Asp Leu Lys Lys Ile Leu Asp Lys Ser Phe Leu
            595                 600                 605

Asp Asp Lys Thr Asn Glu Gln Ile Ile Glu Asp Ile Val Leu Thr Leu
610                 615                 620

Thr Leu Phe Glu Asp Arg Asp Met Ile His Glu Arg Leu Gln Lys Tyr
625                 630                 635                 640

Ser Asp Phe Phe Thr Ser Gln Gln Leu Lys Lys Leu Glu Arg Arg His
                645                 650                 655

Tyr Thr Gly Trp Gly Arg Leu Ser Tyr Lys Leu Ile Asn Gly Ile Arg
            660                 665                 670

Asn Lys Glu Asn Asn Lys Thr Ile Leu Asp Phe Leu Ile Asp Asp Gly
                675                 680                 685

His Ala Asn Arg Asn Phe Met Gln Leu Ile Asn Asp Glu Ser Leu Ser
690                 695                 700

Phe Lys Thr Ile Ile Gln Glu Ala Gln Val Val Gly Asp Val Asp Asp
705                 710                 715                 720

Ile Glu Ala Val Val His Asp Leu Pro Gly Ser Pro Ala Ile Lys Lys
                725                 730                 735

Gly Ile Leu Gln Ser Val Lys Ile Val Asp Glu Leu Val Lys Val Met
            740                 745                 750

Gly Asp Asn Pro Asp Asn Ile Val Ile Glu Met Ala Arg Glu Asn Gln
                755                 760                 765

Thr Thr Gly Tyr Gly Arg Asn Lys Ser Asn Gln Arg Leu Lys Arg Leu
770                 775                 780

Gln Asp Ser Leu Lys Glu Phe Gly Ser Asp Ile Leu Ser Lys Lys Lys
785                 790                 795                 800

Pro Ser Tyr Val Asp Ser Lys Val Glu Asn Ser His Leu Gln Asn Asp
                805                 810                 815

Arg Leu Phe Leu Tyr Tyr Ile Gln Asn Gly Lys Asp Met Tyr Thr Gly
            820                 825                 830

Glu Glu Leu Asp Ile Asp Arg Leu Ser Asp Tyr Asp Ile Asp His Ile
            835                 840                 845

Ile Pro Gln Ala Phe Ile Lys Asp Asn Ser Ile Asp Asn Lys Val Leu
850                 855                 860

Thr Ser Ser Ala Lys Ala Arg Gly Lys Ser Asp Asp Val Pro Ser Ile
865                 870                 875                 880

Glu Ile Val Arg Asn Arg Arg Ser Tyr Trp Tyr Lys Leu Tyr Lys Ser
                885                 890                 895

Gly Leu Ile Ser Lys Arg Lys Phe Asp Asn Leu Thr Lys Ala Glu Arg
            900                 905                 910

Gly Gly Leu Thr Glu Ala Asp Lys Ala Gly Phe Ile Lys Arg Gln Leu
            915                 920                 925

Val Glu Thr Arg Gln Ile Thr Lys His Val Ala Gln Ile Leu Asp Ala
            930                 935                 940

Arg Phe Asn Thr Lys Arg Asp Glu Asn Asp Lys Val Ile Arg Asp Val
945                 950                 955                 960

Lys Val Ile Thr Leu Lys Ser Asn Leu Val Ser Gln Phe Arg Lys Glu
                965                 970                 975

Phe Lys Phe Tyr Lys Val Arg Glu Ile Asn Asp Tyr His His Ala His
            980                 985                 990
```

```
Asp Ala Tyr Leu Asn Ala Val Val Gly Thr Ala Leu Leu Lys Lys Tyr
        995                 1000                1005

Pro Lys Leu Thr Pro Glu Phe Val Tyr Gly Glu Tyr Lys Lys Tyr
    1010                1015                1020

Asp Val Arg Lys Leu Ile Ala Lys Ser Ser Asp Tyr Ser Glu
    1025                1030            1035

Met Gly Lys Ala Thr Ala Lys Tyr Phe Phe Tyr Ser Asn Leu Met
    1040                1045                1050

Asn Phe Phe Lys Thr Glu Val Lys Tyr Ala Asp Gly Arg Val Phe
    1055                1060                1065

Glu Arg Pro Asp Ile Glu Thr Asn Ala Asp Gly Glu Val Val Trp
    1070                1075                1080

Asn Lys Gln Lys Asp Phe Asp Ile Val Arg Lys Val Leu Ser Tyr
    1085                1090                1095

Pro Gln Val Asn Ile Val Lys Lys Val Glu Ala Gln Thr Gly Gly
    1100                1105                1110

Phe Ser Lys Glu Ser Ile Leu Ser Lys Gly Asp Ser Asp Lys Leu
    1115                1120                1125

Ile Pro Arg Lys Thr Lys Lys Val Tyr Trp Asn Thr Lys Lys Tyr
    1130                1135                1140

Gly Gly Phe Asp Ser Pro Thr Val Ala Tyr Ser Val Leu Val Val
    1145                1150                1155

Ala Asp Ile Glu Lys Gly Lys Ala Lys Lys Leu Lys Thr Val Lys
    1160                1165                1170

Glu Leu Val Gly Ile Ser Ile Met Glu Arg Ser Phe Phe Glu Glu
    1175                1180                1185

Asn Pro Val Ser Phe Leu Glu Lys Lys Gly Tyr His Asn Val Gln
    1190                1195                1200

Glu Asp Lys Leu Ile Lys Leu Pro Lys Tyr Ser Leu Phe Glu Phe
    1205                1210                1215

Glu Gly Gly Arg Arg Arg Leu Leu Ala Ser Ala Thr Glu Leu Gln
    1220                1225                1230

Lys Gly Asn Glu Val Met Leu Pro Ala His Leu Val Glu Leu Leu
    1235                1240                1245

Tyr His Ala His Arg Ile Asp Ser Phe Asn Ser Thr Glu His Leu
    1250                1255                1260

Lys Tyr Val Ser Glu His Lys Lys Glu Phe Glu Lys Val Leu Ser
    1265                1270                1275

Cys Val Glu Asn Phe Ser Asn Leu Tyr Val Asp Val Glu Lys Asn
    1280                1285                1290

Leu Ser Lys Val Arg Ala Ala Glu Ser Met Thr Asn Phe Ser
    1295                1300            1305

Leu Glu Glu Ile Ser Ala Ser Phe Ile Asn Leu Leu Thr Leu Thr
    1310                1315                1320

Ala Leu Gly Ala Pro Ala Asp Phe Asn Phe Leu Gly Glu Lys Ile
    1325                1330                1335

Pro Arg Lys Arg Tyr Thr Ser Thr Lys Glu Cys Leu Ser Ala Thr
    1340                1345                1350

Leu Ile His Gln Ser Val Thr Gly Leu Tyr Glu Thr Arg Ile Asp
    1355                1360                1365

Leu Ser Lys Leu Gly Glu Glu
    1370                1375
```

```
<210> SEQ ID NO 7
<211> LENGTH: 36
<212> TYPE: DNA
<213> ORGANISM: Artificial Sequence
<220> FEATURE:
<223> OTHER INFORMATION: NATIVE CRISPR REPEAT

<400> SEQUENCE: 7
gttttagagc tgtgttgttt cgaatggttc caaaac                                 36

<210> SEQ ID NO 8
<211> LENGTH: 87
<212> TYPE: DNA
<213> ORGANISM: Artificial Sequence
<220> FEATURE:
<223> OTHER INFORMATION: NATIVE TRACR RNA

<400> SEQUENCE: 8
ggtttgaaac cattcgaaac aatacagcaa agttaaaata aggctagtcc gtatacaacg       60
tgaaaacacg tggcaccgat tcggtgc                                           87

<210> SEQ ID NO 9
<211> LENGTH: 123
<212> TYPE: DNA
<213> ORGANISM: Artificial Sequence
<220> FEATURE:
<223> OTHER INFORMATION: SGRNA2019V1

<400> SEQUENCE: 9
gttttagagc tgtgttgttt cgaatggttc caaaacggtt tgaaaccatt cgaaacaata       60
cagcaaagtt aaaataaggc tagtccgtat acaacgtgaa acacgtggc accgattcgg       120 tgc                                                                    123

<210> SEQ ID NO 10
<211> LENGTH: 91
<212> TYPE: DNA
<213> ORGANISM: Artificial Sequence
<220> FEATURE:
<223> OTHER INFORMATION: SGRNA2019V2

<400> SEQUENCE: 10
gttttagagc tgtgttgtaa aaacaataca gcaaagttaa aataaggcta gtccgtatac       60
aacgtgaaaa cacgtggcac cgattcggtg c                                      91

<210> SEQ ID NO 11
<211> LENGTH: 90
<212> TYPE: DNA
<213> ORGANISM: Artificial Sequence
<220> FEATURE:
<223> OTHER INFORMATION: SGRNA2019V3

<400> SEQUENCE: 11
gttttagagc tgtgttgtaa aaacaataca gcaagttaaa ataaggctag tccgtataca       60
acgtgaaaac acgtggcacc gattcggtgc                                        90

<210> SEQ ID NO 12
<211> LENGTH: 36
<212> TYPE: DNA
<213> ORGANISM: Artificial Sequence
<220> FEATURE:
<223> OTHER INFORMATION: NATIVE CRISPR REPEAT 2017

<400> SEQUENCE: 12
```

```
gttttagagc tgtgctgttt cgaatggttc caaaac                                     36
```

<210> SEQ ID NO 13
<211> LENGTH: 87
<212> TYPE: DNA
<213> ORGANISM: Artificial Sequence
<220> FEATURE:
<223> OTHER INFORMATION: NATIVE TRACR RNA 2017

<400> SEQUENCE: 13

```
tgttggaact attcgaaaca acacagcgag ttaaataag gctttgtccg tacacaactt            60
gtaaaagggg cacccgattc gggtgca                                              87
```

<210> SEQ ID NO 14
<211> LENGTH: 101
<212> TYPE: DNA
<213> ORGANISM: Artificial Sequence
<220> FEATURE:
<223> OTHER INFORMATION: SGRNA2017V2

<400> SEQUENCE: 14

```
gttttagagc tgtgctgttt cgaaaaatcg aaacaacaca gcgagttaaa ataaggcttt           60
gtccgtacac aacttgtaaa agggcaccc gattcgggtg c                              101
```

<210> SEQ ID NO 15
<211> LENGTH: 91
<212> TYPE: DNA
<213> ORGANISM: Artificial Sequence
<220> FEATURE:
<223> OTHER INFORMATION: SGRNA2017V3

<400> SEQUENCE: 15

```
gttttagagc tgtgctgtaa aaacaacaca gcgagttaaa ataaggcttt gtccgtacac           60
aacttgtaaa agggcaccc gattcgggtg c                                          91
```

<210> SEQ ID NO 16
<211> LENGTH: 83
<212> TYPE: DNA
<213> ORGANISM: Artificial Sequence
<220> FEATURE:
<223> OTHER INFORMATION: SGRNA2017V4

<400> SEQUENCE: 16

```
gttttagagc tgtgcaaaca cagcgagtta aataaggct tgtccgtac acaacttgta            60 aaagggcac ccgattcggg tgc                                                   83
```

<210> SEQ ID NO 17
<211> LENGTH: 83
<212> TYPE: DNA
<213> ORGANISM: Artificial Sequence
<220> FEATURE:
<223> OTHER INFORMATION: SGRNA2019V2-1

<400> SEQUENCE: 17

```
gttttagagc tgtggaaata cagcaaagtt aaaataaggc tagtccgtat acaacgtgaa           60
aacacgtggc accgattcgg tgc                                                  83
```

<210> SEQ ID NO 18
<211> LENGTH: 79
<212> TYPE: DNA
<213> ORGANISM: Artificial Sequence
<220> FEATURE:

```
<223> OTHER INFORMATION: SGRNA2019V2-2

<400> SEQUENCE: 18
gttttagagc tggaaacagc aaagttaaaa taaggctagt ccgtatacaa cgtgaaaaca      60
cgtggcaccg attcggtgc                                                  79

<210> SEQ ID NO 19
<211> LENGTH: 79
<212> TYPE: DNA
<213> ORGANISM: Artificial Sequence
<220> FEATURE:
<223> OTHER INFORMATION: SGRNA2019V2-3

<400> SEQUENCE: 19
gtttaagagc tggaaacagc aaagtttaaa taaggctagt ccgtatacaa cgtgaaaaca      60
cgtggcaccg attcggtgc                                                  79

<210> SEQ ID NO 20
<211> LENGTH: 79
<212> TYPE: DNA
<213> ORGANISM: Artificial Sequence
<220> FEATURE:
<223> OTHER INFORMATION: SGRNA2019V2-4

<400> SEQUENCE: 20
gttatagagc tggaaacagc aaagttataa taaggctagt ccgtatacaa cgtgaaaaca      60
cgtggcaccg attcggtgc                                                  79

<210> SEQ ID NO 21
<211> LENGTH: 79
<212> TYPE: DNA
<213> ORGANISM: Artificial Sequence
<220> FEATURE:
<223> OTHER INFORMATION: SGRNA2019V2-5

<400> SEQUENCE: 21
gtttaagagc tggaaacagc aaagtttaaa taaggctagt ccgtatacaa cgtggaaaca      60
cgtggcaccg attcggtgc                                                  79

<210> SEQ ID NO 22
<211> LENGTH: 79
<212> TYPE: DNA
<213> ORGANISM: Artificial Sequence
<220> FEATURE:
<223> OTHER INFORMATION: SGRNA2019V2-6

<400> SEQUENCE: 22
gttatagagc tggaaacagc aaagttataa taaggctagt ccgtatacaa cgtggaaaca      60
cgtggcaccg attcggtgc                                                  79

<210> SEQ ID NO 23
<211> LENGTH: 79
<212> TYPE: DNA
<213> ORGANISM: Artificial Sequence
<220> FEATURE:
<223> OTHER INFORMATION: SGRNA2019V2-7

<400> SEQUENCE: 23
gtttaagagc tggaaacagc aaagtttaaa taaggctagt ccgtatacaa cgtggaaaca      60
cgtggcaccg attcggtgc                                                  79
```

```
<210> SEQ ID NO 24
<211> LENGTH: 79
<212> TYPE: DNA
<213> ORGANISM: Artificial Sequence
<220> FEATURE:
<223> OTHER INFORMATION: SBRNA2019V2-8

<400> SEQUENCE: 24
gttatagagc tggaaacagc aaagttataa taaggctagt ccgtatacaa cgtggaaaca      60
cgtggcaccg attcggtgc                                                   79

<210> SEQ ID NO 25
<211> LENGTH: 79
<212> TYPE: DNA
<213> ORGANISM: Artificial Sequence
<220> FEATURE:
<223> OTHER INFORMATION: SGRNA2017V4-2

<400> SEQUENCE: 25
gtttaagagc tggaaacagc gagtttaaat aaggctttgt ccgtacacaa cttgtaaaag      60
gggcacccga ttcgggtgc                                                   79

<210> SEQ ID NO 26
<211> LENGTH: 79
<212> TYPE: DNA
<213> ORGANISM: Artificial Sequence
<220> FEATURE:
<223> OTHER INFORMATION: SGRNA2017V4-2-1

<400> SEQUENCE: 26
gtttaagagc tggaaacagc gagtttaaat aaggctttgt ccgtacacaa cttgtaaaag      60
gggcacccga ttcgggtgc                                                   79

<210> SEQ ID NO 27
<211> LENGTH: 79
<212> TYPE: DNA
<213> ORGANISM: Artificial Sequence
<220> FEATURE:
<223> OTHER INFORMATION: SGRNA2017V4-2-2

<400> SEQUENCE: 27
gtttaagagc tggaaacagc gagtttaaat aaggctttgt ccgtacacaa cttgaaaaag      60
gggcacccga ttcgggtgc                                                   79

<210> SEQ ID NO 28
<211> LENGTH: 20
<212> TYPE: DNA
<213> ORGANISM: Artificial Sequence
<220> FEATURE:
<223> OTHER INFORMATION: GUIDE

<400> SEQUENCE: 28
gctgaagcac tgcacgccgt                                                  20

<210> SEQ ID NO 29
<211> LENGTH: 26
<212> TYPE: DNA
<213> ORGANISM: Artificial Sequence
<220> FEATURE:
<223> OTHER INFORMATION: HR IN CREATE FUSION

<400> SEQUENCE: 29
accctcagcc acggcgtgca gtgctt                                           26
```

```
<210> SEQ ID NO 30
<211> LENGTH: 17
<212> TYPE: DNA
<213> ORGANISM: Artificial Sequence
<220> FEATURE:
<223> OTHER INFORMATION: G4 SEQUENCE

<400> SEQUENCE: 30
actaacggtg gtggtgg                                                  17

<210> SEQ ID NO 31
<211> LENGTH: 20
<212> TYPE: DNA
<213> ORGANISM: Artificial Sequence
<220> FEATURE:
<223> OTHER INFORMATION: GUIDE

<400> SEQUENCE: 31
ggtgctgctt catgtggtcg                                               20

<210> SEQ ID NO 32
<211> LENGTH: 54
<212> TYPE: DNA
<213> ORGANISM: Artificial Sequence
<220> FEATURE:
<223> OTHER INFORMATION: HR IN CREATE FUSION

<400> SEQUENCE: 32
accctcagcc acggcgtgca gtgcttcagc cgctatcccg accacatgaa gcag         54
```

NUCLEIC ACID-GUIDED NICKASES

RELATED CASES

This application claims priority to U.S. Ser. No. 63/133,502, filed 4 Jan. 2021, entitled "MAD NUCLEASES", which is incorporated herein in its entirety.

FIELD OF THE INVENTION

The present disclosure provides engineered nucleic acid-guided nickases and optimized scaffolds for making rational, direct edits to nucleic acids in live cells.

INCORPORATION BY REFERENCE

Submitted with the present application is an electronically filed sequence listing via EFS-Web as an ASCII formatted sequence listing, entitled "INSC094US_seq_list_20210818", created Aug. 18, 2021, and 77,000 bytes in size. The sequence listing is part of the specification filed herewith and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development, Recently, various nucleases have been identified that allow manipulation of gene sequence; hence, gene function. These nucleases include nucleic acid-guided nucleases. The range of target sequences that nucleic acid-guided nucleases can recognize, however, is constrained by the need for a specific PAM to be located near the desired target sequence. Providing nucleases with altered PAM preferences and/or altered activity or fidelity may one goal of nuclease engineering. Another goal of engineering nucleic acid-guided nucleases may be to create nickases, which create single-strand breaks rather than double-strande breaks. Such changes may increase the versatility of nucleic acid-guided nucleases for certain editing tasks.

There is thus a need in the art of nucleic acid-guided nuclease gene editing for novel nucleases or nickases with varied PAM preferences, varied activity in cells from different organisms, different cutting motifs and/or altered enzyme fidelity. The novel MAD nickases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

Thus, the present disclosure embodies a nucleic acid-guided nickase selected from the following nickases: MAD2019-H848A, having the amino acid sequence of SEQ ID NO: 3; and MAD2019-N871A, having the amino acid sequence of SEQ ID NO: 4.

In some aspects, the MAD2019-H848A and MAD2019-N871A nickases are in a nucleic acid-guided nickase editing system with a gRNA scaffold having a nucleic acid sequence of SEQ ID NO: 9, SEQ ID NO: 10, SEQ ID NO: 11, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; and in some aspects, the MAD2019-H848A and MAD2019-N871A nickases are in a nucleic acid-guided nickase editing system with a native CRISPR repeat having a nucleic acid sequence of SEQ ID NO: 7 and a native tracr RNA having a nucleic acid sequence of SEQ ID NO:8.

In yet other aspects, the MAD2019-H848A and MAD2019-N871A nickases are in a nucleic acid-guided nickase editing system comprising a guide RNA wherein the guide comprises from 5' to 3' a guide sequence, a homology region and SEQ ID NO: 30.

In addition, the present disclosure embodies a nucleic acid-guided nickase selected from the following nickases: MAD2017-H871A, having the amino acid sequence of SEQ ID NO: 5; and MAD2017-N870A, having the amino acid sequence of SEQ ID NO: 6.

In some aspects of this embodiment, the MAD2017-H871A and MAD2017-N870A nickases are in a nucleic acid-guided nickase editing system with a gRNA scaffold having a nucleic acid sequence of SEQ ID NO: 14, SEQ ID NO: 15, SEQ ID NO: 16, SEQ ID NO: 25, SEQ ID NO: 26, or SEQ ID NO: 27; and in some aspects, the MAD2017-H871A and MAD2017-N870A nickases are in a nucleic acid-guided nickase editing system with a native CRISPR repeat having a nucleic acid sequence of SEQ ID NO: 12 and a native tracer RNA having a nucleic acid sequence of SEQ ID NO:13.

In yet other aspects, the MAD2017-H871A and MAD2017-N870A nickases are in a nucleic acid-guided nickase editing system comprising a guide RNA wherein the guide comprises from 5' to 3' a guide sequence, a homology region and SEQ ID NO: 30.

These aspects and other features and advantages of the invention are described below in more detail.

Figure 1A:
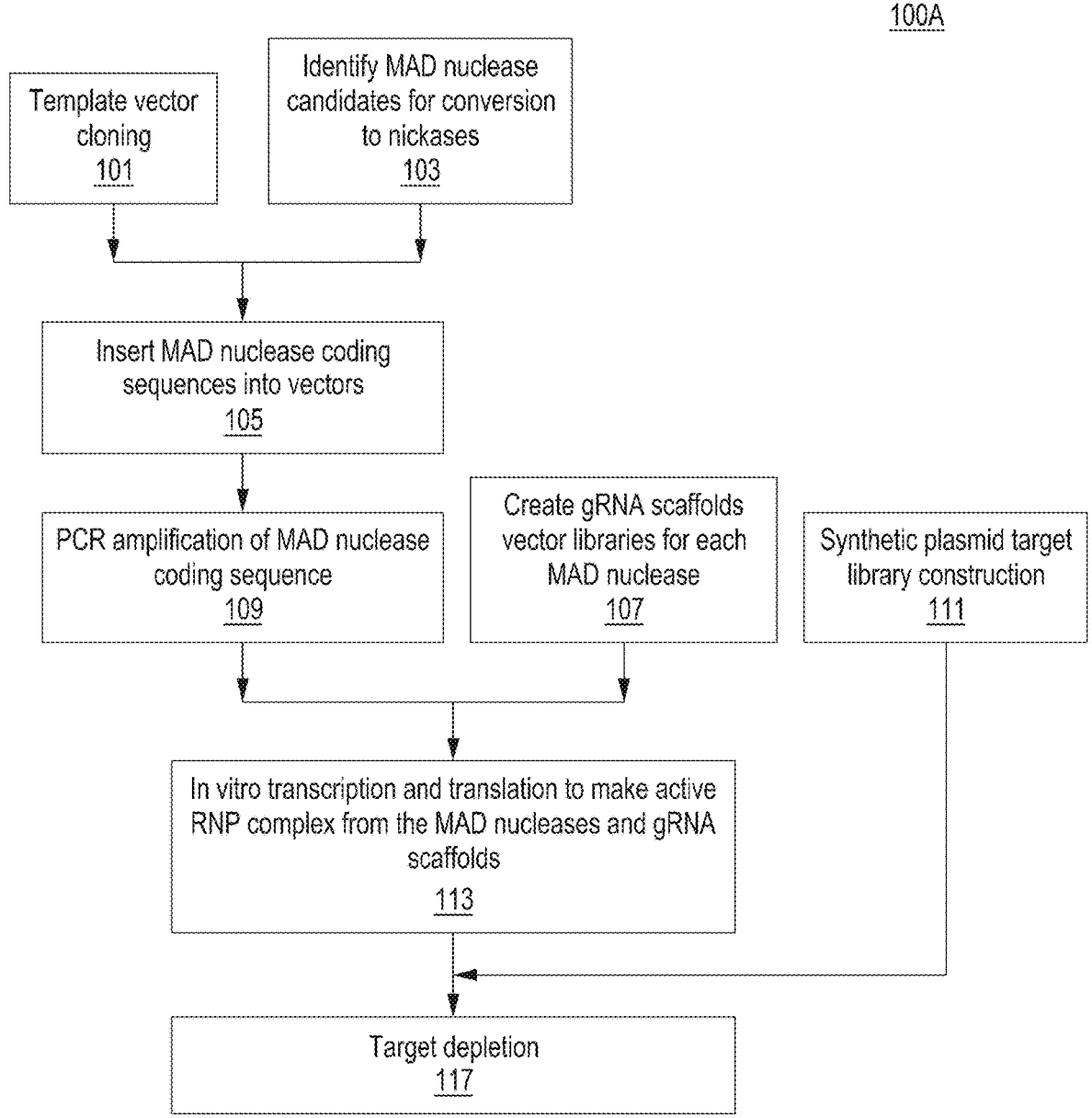
FIGS. 1A and 1B are exemplary workflows for screening for optimized scaffolds to be used with nucleic acid-guided nickases.

It should be understood that the drawings are not necessarily to scale.

DETAILED DESCRIPTION

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry and sequencing technology, which are within the skill of those who practice in the art. Such conventional techniques include polymer array synthesis and hybridization and ligation of polynucleotides. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; *Viral Vectors* (Kaplift & Loewy, eds., Academic Press 1995); all of which are herein incorporated in their entirety by reference for all purposes. For mammalian/stem cell culture and methods see, e.g., *Basic Cell Culture Protocols*, Fourth Ed. (Helgason & Miller, eds., Humana Press 2005); *Culture of Animal Cells*, Seventh Ed. (Freshney, ed., Humana Press 2016); *Microfluidic Cell Culture*, Second Ed. (Borenstein, Vandon, Tao & Charest, eds., Elsevier Press 2018); *Human Cell Culture* (Hughes, ed., Humana Press 2011); 3D Cell Culture (Koledova, ed., Humana Press 2017); *Cell and Tissue Culture: Laboratory Procedures in Biotechnology* (Doyle & Griffiths, eds., John Wiley & Sons 1998); *Essential Stem Cell Methods*, (Lanza & Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza & Atala, eds., Academic Press 2013); and *Handbook of Stem Cells*, (Atala & Lanza, eds., Academic Press 2012). CRISPR-specific techniques can be found in, e.g., *Genome Editing and Engineering from TALENs and CRISPRs to Molecular Surgery*, Appasani and Church (2018); and *CRISPR: Methods and Protocols,* Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

The terms "CREATE fusion enzyme" or the terms "nickase fusion" or "nickase fusion enzyme" refer to a nucleic acid-guided nickase fused to a reverse transcriptase where the fused enzyme both binds and nicks a target sequence in a sequence-specific manner and is capable of utilizing a repair template to incorporate nucleotides into the target sequence at the site of the nick.

The terms "editing cassette", "CREATE cassette", "CREATE editing cassette", "CREATE fusion editing cassette" or "CF editing cassette" refer to a nucleic acid molecule comprising a coding sequence for transcription of a guide nucleic acid or gRNA covalently linked to a coding sequence for transcription of a repair template.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the repair template with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Nucleic acid-guided editing components" refers to one, some, or all of a nucleic acid-guided nuclease or nickase fusion enzyme, a guide nucleic acid and a repair template.

A "PAM mutation" refers to one or more edits to a target sequence that removes, mutates, or otherwise renders inactive a PAM or spacer region in the target sequence.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA. Promoters may be constitutive or inducible.

As used herein the terms "repair template" or "donor nucleic acid" or "donor DNA" or "homology arm" or "HA" or "homology region" or "HR" refer to 1) nucleic acid that is designed to introduce a DNA sequence modification (insertion, deletion, substitution) into a locus by homologous recombination using nucleic acid-guided nucleases, or 2) a nucleic acid that serves as a template (including a desired edit) to be incorporated into target DNA by a reverse transcriptase portion of a nickase fusion enzyme in a CREATE fusion (CF) editing system. For homology-directed repair, the repair template must have sufficient homology to the regions flanking the "cut site" or the site to be edited in the genomic target sequence. For template-directed repair, the repair template has homology to the genomic target sequence except at the position of the desired edit although synonymous edits may be present in the homologous (e.g., non-edit) regions. The length of the repair template(s) will depend on, e.g., the type and size of the modification being made. In many instances and preferably, the repair template will have two regions of sequence homology (e.g., two homology arms) complementary to the genomic target locus flanking the locus of the desired edit in the genomic target locus. Typically, an "edit region" or "edit locus" or "DNA sequence modification" region—the nucleic acid modification that one desires to be introduced into a genome target locus in a cell (e.g., the desired edit)—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "target genomic DNA sequence", "target sequence", or "genomic target locus" and the like refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The terms "transformation", "transfection" and "transduction" are used interchangeably herein to refer to the process of introducing exogenous DNA into cells.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, and the like. In some embodiments, a coding sequence for a nucleic acid-guided nuclease is provided in a vector, referred to as an "engine vector." In some embodiments, the editing cassette may be provided in a vector, referred to as an "editing vector." In some embodiments, the coding sequence for the nucleic acid-guided nuclease and the editing cassette are provided in the same vector.

Nucleic Acid-Guided Nuclease and Nickase Editing

The nucleic acid-guided nickases described herein are employed to allow one to perform nucleic acid nuclease-directed genome editing to introduce desired edits to a population of live mammalian cells. The nucleic acid-guided nickases described herein have been derived from nucleic acid-guided nucleases which were engineered to create a nick as opposed to a double-strand break. In addition to the nickases, gRNA scaffold (sgRNA) sequences have been identified to be used in a nucleic acid-guided nickase CF editing system with the engineered nickases to improve editing efficiency.

Generally, a nucleic acid-guided nuclease or nickase fusion enzyme complexed with an appropriate synthetic guide nucleic acid in a cell can cut the genome of the cell at a desired location. The guide nucleic acid helps the nucleic acid-guided nuclease or nickase fusion enzyme recognize and cut the DNA at a specific target sequence. By manipulating the nucleotide sequence of the guide nucleic acid, the nucleic acid-guided nuclease or nickase fusion enzyme may be programmed to target any DNA sequence for cleavage as long as an appropriate protospacer adjacent motif (PAM) is nearby. In certain aspects, the nucleic acid-guided nuclease system or nucleic acid-guided nickase fusion editing system (i.e., CF editing system) may use two separate guide nucleic acid molecules that combine to function as a guide nucleic acid, e.g., a CRISPR RNA (crRNA) and trans-activating CRISPR RNA (tracrRNA). In other aspects and preferably, the guide nucleic acid is a single guide nucleic acid construct that includes both 1) a guide sequence capable of hybridizing to a genomic target locus, and 2) a scaffold sequence capable of interacting or complexing with a nucleic acid-guided nuclease or nickase fusion enzyme.

In general, a guide nucleic acid (e.g., gRNA) complexes with a compatible nucleic acid-guided nuclease or nickase fusion enzyme and can then hybridize with a target sequence, thereby directing the nuclease or nickase fusion to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. Preferably and typically, the guide nucleic acid comprises RNA and the gRNA is encoded by a DNA sequence on an editing cassette along with the coding sequence for a repair template. Covalently linking the gRNA and repair template allows one to scale up the number of edits that can be made in a population of cells tremendously. Methods and compositions for designing and synthesizing editing cassettes (e.g., CREATE cassettes) are described in U.S. Pat. Nos. 10,240,167; 10,266,849; 9,982,278; 10,351,877; 10,364,442; 10,435,715; 10,669,559; 10,711,284; 10,731,180, all of which are incorporated by reference herein.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease or nickase fusion enzyme to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In general, to generate an edit in the target sequence, the gRNA/nuclease or gRNA/nickase fusion complex binds to a target sequence as determined by the guide RNA, and the nuclease or nickase fusion recognizes a protospacer adjacent motif (PAM) sequence adjacent to the target sequence. The target sequence can be any polynucleotide endogenous or exogenous to the cell, or in vitro. For example, in the case of mammalian cells the target sequence is typically a polynucleotide residing in the nucleus of the cell. A target sequence can be a sequence encoding a gene product (e.g., a protein) or a non-coding sequence (e.g., a regulatory polynucleotide, an intron, a PAM, a control sequence, or "junk" DNA). The proto-spacer mutation (PAM) is a short nucleotide sequence recognized by the gRNA/nuclease complex. The precise preferred PAM sequence and length requirements for different nucleic acid-guided nucleases or nickase fusions vary; however, PAMs typically are 2-10 base-pair sequences adjacent or in proximity to the target sequence and, depending on the nuclease or nickase, can be 5' or 3' to the target sequence.

In most embodiments, genome editing of a cellular target sequence both introduces a desired DNA change (i.e., the desired edit) to a cellular target sequence, e.g., the genomic DNA of a cell, and removes, mutates, or renders inactive a proto-spacer/spacer mutation (PAM) region in the cellular target sequence (e.g., thereby rendering the target site immune to further nuclease binding). Rendering the PAM and/or spacer at the cellular target sequence inactive precludes additional editing of the cell genome at that cellular target sequence, e.g., upon subsequent exposure to a nucleic acid-guided nuclease or nickase fusion complexed with a synthetic guide nucleic acid in later rounds of editing. Thus, cells having the desired cellular target sequence edit and an altered PAM or spacer can be selected for by using a nucleic acid-guided nuclease or nickase fusion complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM or spacer alteration will not be cut, as these edited cells no longer contain the necessary PAM site and will continue to grow and propagate.

As for the nuclease or nickase fusion component of the nucleic acid-guided nuclease editing system, a polynucleotide sequence encoding the nucleic acid-guided nuclease or nickase fusion enzyme can be codon optimized for expression in particular cell types, such as bacterial, yeast, and, here, mammalian cells. The choice of the nucleic acid-guided nuclease or nickase fusion enzyme to be employed depends on many factors, such as what type of edit is to be made in the target sequence and whether an appropriate PAM is located close to the desired target sequence. Nucleic acid-guided nucleases (i.e., CRISPR enzymes) of use in the methods described herein include but are not limited to Cas 9, Cas 12/CpfI, MAD2, or MAD7, MAD 2007 or other MADzymes and MADzyme systems (see U.S. Pat. Nos. 9,982,279; 10,337,028; 10,435,714; 10,011,849; 10,626,416; 10,604,746; 10,665,114; 10,640,754; 10,876,102; 10,883,077; 10,704,033; 10,745,678; 10,724,021; 10,767,169; and 10,870,761 for sequences and other details related to engineered and naturally-occurring MADzymes). Nickase fusion enzymes typically comprise a CRISPR nucleic acid-guided nuclease engineered to cut one DNA strand in a target DNA rather than making a double-stranded cut, and the nickase portion is fused to a reverse transcriptase. For more information on nickases and nickase fusion editing see U.S. Pat. No. 10,689,669 and U.S. Ser. Nos. 16/740,418; 16/740,420 and 16/740,421, all of which were filed 11 Jan. 2020. A coding sequence for a desired nuclease or nickase fusion may be on an "engine vector" along with other desired sequences such as a selective marker or may be transfected into a cell as a protein or ribonucleoprotein ("RNP") complex.

Another component of the nucleic acid-guided nuclease or nickase fusion system is the repair template comprising homology to the cellular target sequence. In some exemplary embodiments, the repair template is in the same editing cassette as (e.g., is covalently-linked to) the guide nucleic acid and typically is under the control of the same promoter as the gRNA (that is, a single promoter driving the transcription of both the editing gRNA and the repair template). The repair template is designed to serve as a template for homologous recombination with a cellular target sequence cleaved by a nucleic acid-guided nuclease or serve as the template for template-directed repair via a nickase fusion, as a part of the gRNA/nuclease complex. A repair template polynucleotide may be of any suitable length, such as about or more than about 20, 25, 50, 75, 100, 150, 200, 500, or 1000 nucleotides in length, and up to 2, 3, 4, 5, 6, 7, 8, 9, 10, 11, 12, 13 and up to 20 kb in length if combined with a dual gRNA architecture as described in U.S. Pat. No. 10,711,284.

In certain preferred aspects, the repair template can be provided as an oligonucleotide of between 20-300 nucleotides, more preferably between 50-250 nucleotides. As described infra, the repair template comprises a region that is complementary to a portion of the cellular target sequence. When optimally aligned, the repair template overlaps with (is complementary to) the cellular target sequence by, e.g., about as few as 4 (in the case of nickase fusions) and as many as 20, 25, 30, 35, 40, 50, 60, 70, 80, 90 or more nucleotides (in the case of nucleases). The repair template comprises a region complementary to the cellular target sequence flanking the edit locus or difference between the repair template and the cellular target sequence. The desired edit may comprise an insertion, deletion, modification, or any combination thereof compared to the cellular target sequence.

As described in relation to the gRNA, the repair template may be provided as part of a rationally-designed editing cassette along with a promoter to drive transcription of both the gRNA and repair template. As described below, the editing cassette may be provided as a linear editing cassette, or the editing cassette may be inserted into an editing vector. Moreover, there may be more than one, e.g., two, three, four, or more editing gRNA/repair template pairs rationally-designed editing cassettes linked to one another in a linear "compound cassette" or inserted into an editing vector; alternatively, a single rationally-designed editing cassette may comprise two to several editing gRNA/repair template pairs, where each editing gRNA is under the control of separate different promoters, separate promoters, or where all gRNAs/repair template pairs are under the control of a single promoter. In some embodiments the promoter driving transcription of the editing gRNA and the repair template (or driving more than one editing gRNA/repair template pair) is an inducible promoter. In many if not most embodiments of the compositions, methods, modules and instruments described herein, the editing cassettes make up a collection or library editing of gRNAs and of repair templates representing, e.g., gene-wide or genome-wide libraries of editing gRNAs and repair templates.

In addition to the repair template, the editing cassettes comprise one or more primer binding sites to allow for PCR amplification of the editing cassettes. The primer binding sites are used to amplify the editing cassette by using oligonucleotide primers, and may be biotinylated or otherwise labeled. In addition, the editing cassette may comprise a barcode. A barcode is a unique DNA sequence that corresponds to the repair template sequence such that the barcode serves as a proxy to identify the edit made to the corresponding cellular target sequence. The barcode typically comprises four or more nucleotides. Also, in preferred embodiments, an editing cassette or editing vector or engine vector further comprises one or more nuclear localization sequences (NLSs), such as about or more than about 1, 2, 3, 4, 5, 6, 7, 8, 9, 10, or more NLSs.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

Figure 1B:
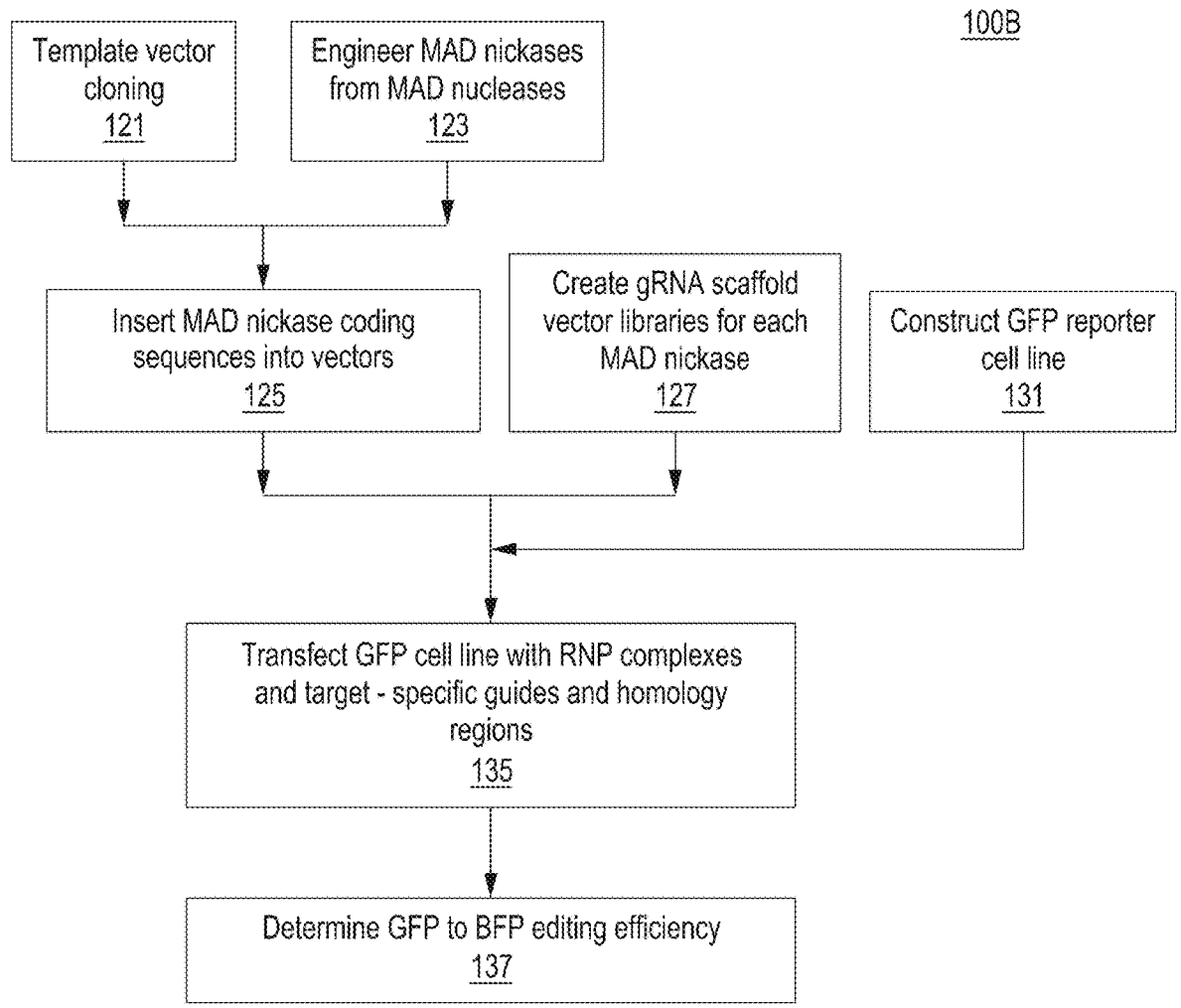

The disclosed MAD nucleic acid-guided nuclease and nickase fusion gRNA scaffolds were identified by the methods depicted in FIGS. 1A and 1B. The gRNA scaffolds form a part of a nucleic acid-guided nickase system for CF editing in cells. FIG. 1A shows an exemplary workflow 100A for screening MAD nucleic acid-guided nuclease and nickase scaffolds by determining cut activity using target depletion. In a first step 103, identified MAD nucleases identified as candidate for engineering. In parallel, a template vector is cloned 101. The coding sequences for the nucleic acid-guided nucleases are inserted into the template vector 105 and the nuclease sequences are amplified by PCR 109. Once the coding sequences for the nuclease are amplified 109, the native CRISPR repeat and tracrRNA for the nucleic acid-guided nuclease are used to construct variations on the gRNA scaffold structure 107 and are inserted into vector backbones. The nucleic acid-guided nucleases and sRNA scaffolds are transcribed, translated and combined to make active ribonucleoprotein (RNP) complexes 113. In parallel, synthetic targets were constructed 111 on which to test the RNP complexes for target depletion 117.

FIG. 1B shows an exemplary workflow 100B for screening of MAD nucleic acid-guided nickase scaffolds. In a first step 123, MAD nucleic acid-guided nucleases are identified as candidates for engineering nucleic acid-guided nickases. In parallel, a template vector is cloned 121. The coding sequences for the nucleic acid-guided nickases are inserted into the template vector 125 and the nuclease sequences are amplified by PCR. Once the coding sequences for the nickase are amplified, the native CRISPR repeat and tracrRNA for the nucleic acid-guided nuclease upon which the nickase is based are used to construct variations on the gRNA scaffold structure 127 and are inserted into vector backbones. The nucleic acid-guided nickases and gRNA scaffolds are transcribed, translated and combined to make active ribonucleoprotein (RNP) complexes. In parallel, a GFP reporter cell line is constructed 131. At step 135, the GFP reporter cell line is transfected with the RNP complexes and target-specific guides and homology regions. Finally, GFP to BFP editing efficiency 137 is determined.

Table 1 shows the amino acid sequences for the MAD2019 and MAD2017 nucleases on which the nickases are based (SEQ ID NO:1 and SEQ ID NO:2, respectively), as well as two nickases derived from each of these nucleases; namely, MAD2019-H848A (SEQ ID NO:3); MAD2019-N871A (SEQ ID NO:4); MAD2017-H847A (SEQ ID NO:5); and MAD2017-N870A (SEQ ID NO:6).

TABLE 1

| Sequence Description | Derived from | Amino Acid Sequence |
|---|---|---|
| MAD2019 nuclease | *Streptococcus sp.* (*firmicutes*) | MTKPYSIGLDIGTNSVGWAVITDDYKVPSKKMKVLGNTSKKYIKKNLLGALLFDSGITAEGRRL KRTARRRYTRRRNRILYLQEIFSTEMATLDDAFFQRLDDSFLVPDDKRDSKYPIFGNLVEEKAY HDEFPTIYHLRKYLADSTKKADLRLVYLALAHMIKYRGHFLIEGEFNSKNNDIQKNFQDFLDTY NAIFESDLSLENSKQLEEIVKDKISKLEKKDRILKLFPGEKNSGIFSEFLKLIVGNQADFKKYFNLD EKASLHFSKESYDEDLETLLGYIGDDYSDVFLKAKKLYDAILLSGILTVTDNGTETPLSSAMIMRY KEHEEDLGLLKAYIRNISLKTYNEVFNDDTKNGYAGYIDGKTNQEDFYVYLKKLLAKFEGADYF LEKIDREDFLRKQRTFDNGSIPYQIHLQEMRAILDKQAKFYPFLAKNKERIEKILTFRIPYYVGPL ARGNSDFAWSIRKRNEKITPWNFEDVIDKESSAEAFINRMTSFDLYLPEEKVLPKHSLLYETFT VYNELTKVRFIAEGMSDYQFLDSKQKKDIVRLYFKGKRKVKVTDKDIIEYLHAIDGYDGIELKGI EKQFNSSLSTYHDLLNIINDKEFLDDSSNEAIIEEIIHTLTIFEDREMIKQRLSKFENIFDKSVLKKLS RRHYTGWGKLSAKLINGIRDEKSGNTILDYLIDDGISNRNFMQLIHDDALSFKKKIQKAQIIGD KDKDNIKEVVKSLPGSPAIKKGILQSIKIVDELVKVMGRKPESIVVEMARENQYTNQGKSNSQ QRLKRLEESLEELGSKILKENIPAKLSKIDNNSLQNDRLYLYYLQNGKDMYTGDDLDIDRLSNYD IDHIIPQAFLKDNSIDNKVLVSSASNRGKSDDVPSLEVVKKRKTLWYQLLKSKLISQRKFDNLTK AERGGLSPEDKAGFIQRQLVETRQITKHVARLLDEKFNNKKDENNRAVRTVKIITLKSTLVSQF RKDFELYKVREINDFHHAHDAYLNAVVASALLKKYPKLEPEFVYGDYPKYNSFRERKSATEKVY FYSNIMNIFKKSISLADGRVIERPLIEVNEETGESVWNKESDLATVRRVLSYPQVNVVKKVEVQ SGGFSKELVQPHGNSDKLIPRKTKKMIWDTKKYGGFDSPIVAYSVLVMAEREKGKSKKLKPVK ELVRITIMEKESFKENTIDFLERRGLRNIQDENIILLPKFSLFELENGRRRLLASAKELQKGNEFILP NKLVKLLYHAKNIHNTLEPEHLEYVESHRADFGKILDVVSVFSEKYILAEAKLEKIKEIYRKNMNT EIHEMATAFINLLTFTSIGAPATFKFFGHNIERKRYSSVAEILNATLIHQSVTGLYETRIDLGKLGE D [SEQ ID NO: 1] |
| MAD2017 nuclease | *Streptococcus sp.* (*firmicutes*) | MKKPYSIGLDIGTNSVGWAVITDDYKVPAKKMKVLGNTDKKYIKKNLLGALLFDSGETAEVTR LKRTARRRYTRRKNRLRYLQEIFAKEMTKVDESFFQRLEESFLTDDDKTFDSHPIFGNKAEEDA YHQKFPTIYHLRKYLADSQEKADLRLVYLALAHMIKYRGHFLIEGELNAENTDVQKLFNVFVET YDKIVDESHLSEIEVDASSILTEKVSKSRRLENLIKQYPTEKKNTLFGNLIALALGLQPNFKTNFKL SEDAKLQFSKDTYEEDLEELLGKVGDDYADLFISAKNLYDAILLSGILTVHDNSTKAPLSASMIK RYVEHHEDLEKLKEFIKINKLKLYHDIFKDKTKNGYAGYIDNGVKQDEFYKYLKTILTKIDDSDYF LDKIERDDFLRKQRTFDNGSIPHQIHLQEMHSILRRQGEYYPFLKENQAKIEKILTFRIPYYVGPL ARKDSRFAWANYHSDEPITPWNFDEVVDKEKSAEKFITRMTLNDLYLPEEKVLPKHSHVYETF TVYNELTKIKYVNEQGESFFFDANMKQEIFDHVFKENRKVTKAKLLSYLNNEFEEFRINDLIGL DKDSKSFNASLGTYHDLKKILDKSFLDDKTNEQIIEDIVLTLTLFEDRDMIHERLQKYSDFFTSQ QLKKLERRHYTGWGRLSYKLINGIRNKENNKTILDFLIDDGHANRNFMQLINDESLSFKTIIQE AQVVGDVDDIEAVVHDLPGSPAIKKGILQSVKIVDELVKVMGDNPDNIVIEMARENQTTGYG RNKSNQRLKRLQDSLKEFGSDILSKKKPSYVDSKVENSHLQNDRLFLYYIQNGKDMYTGEELDI DRLSDYDIDHIIPQAFIKDNSIDNKVLTSSAKNRGKSDDVPSIEIVRNRRSYWYKLYKSGLISKRK FDNLTKAERGGLTEADKAGFIKRQLVETRQITKHVAQILDARFNTKRDENDKVIRDVKVITLKS NLVSQFRKEFKFYKVREINDYHHANDAYLNAVVGTALLKKYPKLTPEFVYGEYKKYDVRKLIAK SSDDYSEMGKATAKYFFYSNLMNFFKTEVKYADGRVFERPDIETNADGEVVWNKQKDFDIV RKVLSYPQVNIVKKVEAQTGGFSKESILSKGDSDKLIPRKTKKVYWNTKKYGGFDSPTVAYSVL VVADIEKGKAKKLKTVKELVGISIMERSFFEENPVSFLEKKGYHNVQEDKLIKLPKYSLFEFEGG RRRLLASATELQKGNEVMLPAHLVELLYHAHRIDSFNSTEHLKYVSEHKKEFEKVLSCVENFSN LYVDVEKNLSKVRAAAESMTNFSLEEISASFINLLTLTALGAPADFNFLGEKIPRKRYTSTKECLS ATLIHQSVTGLYETRIDLSKLGEE [SEQ ID NO: 2] |
| MAD2019 Nickase H848A | *Streptococcus sp.* (*firmicutes*) then engineered | MTKPYSIGLDIGTNSVGWAVITDDYKVPSKKMKVLGNTSKKYIKKNLLGALLFDSGITAEGRRL KRTARRRYTRRRNRILYLQEIFSTEMATLDDAFFQRLDDSFLVPDDKRDSKYPIFGNLVEEKAY HDEFPTIYHLRKYLADSTKKADLRLVYLALAHMIKYRGHFLIEGEFNSKNNDIQKNFQDFLDTY NAIFESDLSLENSKQLEEIVKDKISKLEKKDRILKLFPGEKNSGIFSEFLKLIVGNQADFKKYFNLD EKASLHFSKESYDEDLETLLGYIGDDYSDVFLKAKKLYDAILLSGILTVTDNGTETPLSSAMIMRY KEHEEDLGLLKAYIRNISLKTYNEVFNDDTKNGYAGYIDGKTNQEDFYVYLKKLLAKFEGADYF LEKIDREDFLRKQRTFDNGSIPYQIHLQEMRAILDKQAKFYPFLAKNKERIEKILTFRIPYYVGPL ARGNSDFAWSIRKRNEKITPWNFEDVIDKESSAEAFINRMTSFDLYLPEEKVLPKHSLLYETFT VYNELTKVRFIAEGMSDYQFLDSKQKKDIVRLYFKGKRKVKVTDKDIIEYLHAIDGYDGIELKGI EKQFNSSLSTYHDLLNIINDKEFLDDSSNEAIIEEIIHTLTIFEDREMIKQRLSKFENIFDKSVLKKLS RRHYTGWGKLSAKLINGIRDEKSGNTILDYLIDDGISNRNFMQLIHDDALSFKKKIQKAQIIGD KDKDNIKEVVKSLPGSPAIKKGILQSIKIVDELVKVMGRKPESIVVEMARENQYTNQGKSNSQ QRLKRLEESLEELGSKILKENIPAKLSKIDNNSLQNDRLYLYYLQNGKDMYTGDDLDIDRLSNYD IDAIIPQAFLKDNSIDNKVLVSSASNRGKSDDVPSLEVVKKRKTLWYQLLKSKLISQRKFDNLTK AERGGLSPEDKAGFIQRQLVETRQITKHVARLLDEKFNNKKDENNRAVRTVKIITLKSTLVSQF RKDFELYKVREINDFHHANDAYLNAVVASALLKKYPKLEPEFVYGDYPKYNSFRERKSATEKVY |

TABLE 1-continued

| Sequence Description | Derived from | Amino Acid Sequence |
|---|---|---|
| | | FYSNIMINIFKKSISLADGRVIERPLIEVNEETGESVWNKESDLATVRRVLSYPQVNVVKKVEVQ<br>SGGGFSKELVQPHGNSDKLIPRKTKKMIWDTKKYGGFDSPIVAYSVLVMAEREKGKSKKLKPVK<br>ELVRITIMEKESFKENTIDFLERRGLRNIQDENIILLPKFSLFELENGRRRLLASAKELQKGNEFILP<br>NKLVKLLYHAKNIHNTLEPEHLEYVESHRADFGKILDVVSVFSEKYILAEAKLEKIKEIYRKNMNT<br>EIHEMATAFINLLTFTSIGAPATFKFFGHNIERKRYSSVAEILNATLIHQSVTGLYETRIDLGKLGE<br>D<br>[SEQ ID NO: 3] |
| MAD2019 Nickase N871A | Streptococcus sp. (firmicutes) then engineered) | MTKPYSIGLDIGTNSVGWAVITDDYKVPSKKMKVLGNTSKKYIKKNLLGALLFDSGITAEGRRL<br>KRTARRRYTRRRNRILYLQEIFSTEMATLDDAFFQRLDDSFLVPDDKRDSKYPIFGNLVEEKAY<br>HDEFPTIYHLRKYLADSTKKADLRLVYLALAHMIKYRGHFLIEGEFNSKNNDIQKNFQDFLDTY<br>NAIFESDLSLENSKQLEEIVKDKISKLEKKDRILKLFPGEKNSGIFSEFLKLIVGNQADFKKYFNLD<br>EKASLHFSKESYDEDLETLLGYIGDDYSDVFLKAKKLYDAILLSGILTVTDNGTETPLSSAMIMRY<br>KEHEEDLGLLKAYIRNISLKTYNEVFNDDTKNGYAGYIDGKTNQEDFYVYLKKLLAKFEGADYF<br>LEKIDREDFLRKQRTFDNGSIPYQIHLQEMRAILDKQAKFYPPFLAKNKERIEKILTFRIPYYVGPL<br>ARGNSDFAWSIRKRNEKITPWNFEDVIDKESSAEAFINRMTSFDLYLPEEKVLPKHSLLYETFT<br>VYNELTKVRFIAEGMSDYQFLDSKQKKDIVRLYFKGRKVKVTDKDIIEYLHAIDGYDGIELKGI<br>EKQFNSSLSTYHDLLNIINDKEFLDDSSNEAIIEEIIHTLTIFEDREMIKQRLSKFENIFDKSVLKKLS<br>RRHYTGWGKLSAKLINGIRDEKSGNTILDYLIDDGISNRNFMQLIHDDALSFKKKIQKAQIIGD<br>KDKDNIKEVVKSLPGSPAIKKGILQSIKIVDELVKVMGRKPESIVVEMARENQYTNQGKSNSQ<br>QRLKRLEESLEELGSKILKENIPAKLSKIDNNRLYLYQNGKDMYTGDDLDIDRLSNYD<br>IDHIIPQAFLKDNSIDNKVLVSSASARGKSDDVPSLEVVKKRKTLWYQLLKSKLISQRKFDNLTK<br>AERGGLSPEDKAGFIQRQLVETRQITKHVARLLDEKFNNKKDENNRAVRTVKIITLKKSTLVSQF<br>RKDFELYKVREINDFHHANDAYLNAVVASALLKKYPKLEPEFVYGDYPKYNSFRERKSATEKVY<br>FYSNIMINIFKKSISLADGRVIERPLIEVNEETGESVWNKESDLATVRRVLSYPQVNVVKKVEVQ<br>SGGGFSKELVQPHGNSDKLIPRKTKKMIWDTKKYGGFDSPIVAYSVLVMAEREKGKSKKLKPVK<br>ELVRITIMEKESFKENTIDFLERRGLRNIQDENIILLPKFSLFELENGRRRLLASAKELQKGNEFILP<br>NKLVKLLYHAKNIHNTLEPEHLEYVESHRADFGKILDVVSVFSEKYILAEAKLEKIKEIYRKNMNT<br>EIHEMATAFINLLTFTSIGAPATFKFFGHNIERKRYSSVAEILNATLIHQSVTGLYETRIDLGKLGE<br>D<br>[SEQ ID NO: 4] |
| MAD2017 nickase H847A | Streptococcus sp. (firmicutes) then engineered) | MKKPYSIGLDIGTNSVGWAVITDDYKVPAKKMKVLGNTDKKYIKKNLLGALLFDSGETAEVTR<br>LKRTARRRYTRRKNRLRYLQEIFAKEMTKVDESFFQRLEESFLTDDDKTFDSHPIFGNKAEEDA<br>YHQKFPTIYHLRKYLADSQEKADLRLVYLALAHMIKYRGHFLIEGELNAENTDVQKLFNVFVET<br>YDKIVDESHLSEIEVDASSILTEKVSKSRRLENLIKQYPTEKKNTLFGNLIALALGLQPNFKTNFKL<br>SEDAKLQFSKDTYEEDLEELLGKVGDDYADLFISAKNLYDAILLSGILTVDDNSTKAPLSASMIK<br>RYVEHHEDLEKLKEFIKINKLKLYHDIFKDKTKNGYAGYIDNGVKQDEFYKYLKTILTKIDDSDYF<br>LDKIERDDFLRKQRTFDNGSIPHQIHLQEMHSILRRQGEYYPFLKENQAKIEKILTFRIPYYVGPL<br>ARKDSRFAWANYHSDEPITPWNFDEVVDKEKSAEKFITRMTLNDLYLPEEKVLPKHSVYETF<br>TVYNELTKIKYVNEQGESFFFDANMKQEIFDHVFKENRKVTKAKLLSYLNNEFEEFRINDLIGL<br>DKDSKSFNASLGTYHDLKKILDKSFLDDKTNEQIIEDIVLTLTLFEDRDMIHERLQKYSDFFTSQ<br>QLKKLERRHYTGWGRLSYKLINGIRNKENNKTILDFLIDDGHANRNFMQLINDESLSFKTIIQE<br>AQVVGDVDDIEAVVHDLPGSPAIKKGILQSVKIVDELVKVMGDNPDNIVIEMARENQTTGYG<br>RNKSNQRLKRLQDSLKEFGSDILSKKKPSYVDSKVENSHLQNDRLFLYYIQNGKDMYTGEELDI<br>DRLSDYDIDAIIPQAFIKDNSIDNKVLTSSAKNRGKSDDVPSIEIVRNRRSYWYKLYKSGLISKRK<br>FDNLTKAERGGLSTEADKAGFIKRQLVETRQITKHVAQILDARFNTKRDENDKVIRDVKVITLKS<br>NLVSQFRKEFKFYKVREINDYHHAHDAYLNAVVGTALLKKYPKLTPEFVGEYKKYDVRKLIAK<br>SSDDYSEMGKATAKYFFYSNLMNFFKTEVKYADGRVFERPDIETNADGEVVWNKQKDFDIV<br>RKVLSYPQVNIVKKVEAQTGGFSKESILSKGSDKLIPRKTKKVYWNTKKYGGFDSPTVAYSVL<br>VVADIEKGKAKKLKTVKELVGISIMERSFFEENPVSFLEKKGYHNVQEDKLIKLPKYSLFEFEGG<br>RRRLLASATELQKGNEVMLPAHLVELLYHAHRIDSFNSTEHLKYVSEHKKEFEKVLSCVENFSN<br>LYVDVEKNLSKVRAAAESMTNFSLEEISASFINLLTLTALGAPADFNLGEKIPRKRYTSTKECLS<br>ATLIHQSVTGLYETRIDLSKLGEE<br>[SEQ ID NO: 5] |
| MAD2017 nickase N870A | Streptococcus sp. (firmicutes) then engineered | MKKPYSIGLDIGTNSVGWAVITDDYKVPAKKMKVLGNTDKKYIKKNLLGALLFDSGETAEVTR<br>LKRTARRRYTRRKNRLRYLQEIFAKEMTKVDESFFQRLEESFLTDDDKTFDSHPIFGNKAEEDA<br>YHQKFPTIYHLRKYLADSQEKADLRLVYLALAHMIKYRGHFLIEGELNAENTDVQKLFNVFVET<br>YDKIVDESHLSEIEVDASSILTEKVSKSRRLENLIKQYPTEKKNTLFGNLIALALGLQPNFKTNFKL<br>SEDAKLQFSKDTYEEDLEELLGKVGDDYADLFISAKNLYDAILLSGILTVDDNSTKAPLSASMIK<br>RYVEHHEDLEKLKEFIKINKLKLYHDIFKDKTKNGYAGYIDNGVKQDEFYKYLKTILTKIDDSDYF<br>LDKIERDDFLRKQRTFDNGSIPHQIHLQEMHSILRRQGEYYPFLKENQAKIEKILTFRIPYYVGPL<br>ARKDSRFAWANYHSDEPITPWNFDEVVDKEKSAEKFITRMTLNDLYLPEEKVLPKHSVYETF<br>TVYNELTKIKYVNEQGESFFFDANMKQEIFDHVFKENRKVTKAKLLSYLNNEFEEFRINDLIGL<br>DKDSKSFNASLGTYHDLKKILDKSFLDDKTNEQIIEDIVLTLTLFEDRDMIHERLQKYSDFFTSQ<br>QLKKLERRHYTGWGRLSYKLINGIRNKENNKTILDFLIDDGHANRNFMQLINDESLSFKTIIQE<br>AQVVGDVDDIEAVVHDLPGSPAIKKGILQSVKIVDELVKVMGDNPDNIVIEMARENQTTGYG<br>RNKSNQRLKRLQDSLKEFGSDILSKKKPSYVDSKVENSHLQNDRLFLYYIQNGKDMYTGEELDI<br>DRLSDYDIDHIIPQAFIKDNSIDNKVLTSSAKARGKSDDVPSIEIVRNRRSYWYKLYKSGLISKRK<br>FDNLTKAERGGLSTEADKAGFIKRQLVETRQITKHVAQILDARFNTKRDENDKVIRDVKVITLKS<br>NLVSQFRKEFKFYKVREINDYHHAHDAYLNAVVGTALLKKYPKLTPEFVGEYKKYDVRKLIAK<br>SSDDYSEMGKATAKYFFYSNLMNFFKTEVKYADGRVFERPDIETNADGEVVWNKQKDFDIV<br>RKVLSYPQVNIVKKVEAQTGGFSKESILSKGSDKLIPRKTKKVYWNTKKYGGFDSPTVAYSVL<br>VVADIEKGKAKKLKTVKELVGISIMERSFFEENPVSFLEKKGYHNVQEDKLIKLPKYSLFEFEGG<br>RRRLLASATELQKGNEVMLPAHLVELLYHAHRIDSFNSTEHLKYVSEHKKEFEKVLSCVENFSN |

TABLE 1-continued

| Sequence Description | Derived from | Amino Acid Sequence |
|---|---|---|
| | | LYVDVEKNLSKVRAAAESMTNFSLEEISASFINLLTLTALGAPADFNFLGEKIPRKRYTSTKECLS ATLIHQSVTGLYETRIDLSKLGEE [SEQ ID NO: 6] |

Example 2: Scaffold Optimization for the MAD2019 and MAD2017 Nickases

MAD2019 Nuclease:

Three versions of gRNA scaffolds were designed using the MAD2019 nuclease native CRISPR repeat and tracr RNA sequences (corresponding to step 107 of FIG. 1A). The native CRISPR repeat and tracr RNA for the MAD2019 nuclease (SEQ ID NOs: 7 and 8, respectively), as well as the variant gRNA scaffolds (sgRNA) for MAD2019 (i.e., gRNA scaffold 2019v1 [SEQ ID NO:9]; gRNA scaffold 2019v2 [SEQ ID NO:10]; and gRNA scaffold 2019v3 [SEQ ID NO:11]) are shown in Table 2.

TABLE 2

First Round of Scaffold Optimization for MAD2019 Nickase

| Sequence Name | Sequence |
|---|---|
| Native CRISPR repeat MAD2019 | 5'-GTTTTAGAGCTGTGTTGTTTCGAATGGTTCC AAAAC-3' [SEQ ID NO: 7] |
| Native tracr RNA MAD2019 | 5'-GGTTTGAAACCATTCGAAACAATACAGCAAA GTTAAAATAAGGCTAGTCCGTATACAACGTGAAA ACACGTGGCACCGATTCGGTGC-3' [SEQ ID NO: 8] |
| sgRNA2019v1 | 5'-GTTTTAGAGCTGTGTTGTTTCGAATGGTTCC AAAACGGTTTGAAACCATTCGAAACAATACAGCA AGTTAAAATAAGGCTAGTCCGTATACAACGTGA AAACACGTGGCACCGATTCGGTGC-3' [SEQ ID NO: 9] |
| sgRNA2019v2 | 5'-GTTTTAGAGCTGTGTTGTAAAAACAATACAGC AAAGTTAAAATAAGGCTAGTCCGTATACAACGTGA AAACACGTGGCACCGATTCGGTGC-3' [SEQ ID NO: 10] |
| sgRNA2019v3 | 5'-GTTTTAGAGCTGTGTTGTAAAAACAATACAGC AAGTTAAAATAAGGCTAGTCCGTATACAACGTGAA AACACGTGGCACCGATTCGGTGC-3' [SEQ ID NO: 11] |

Figure 2A:
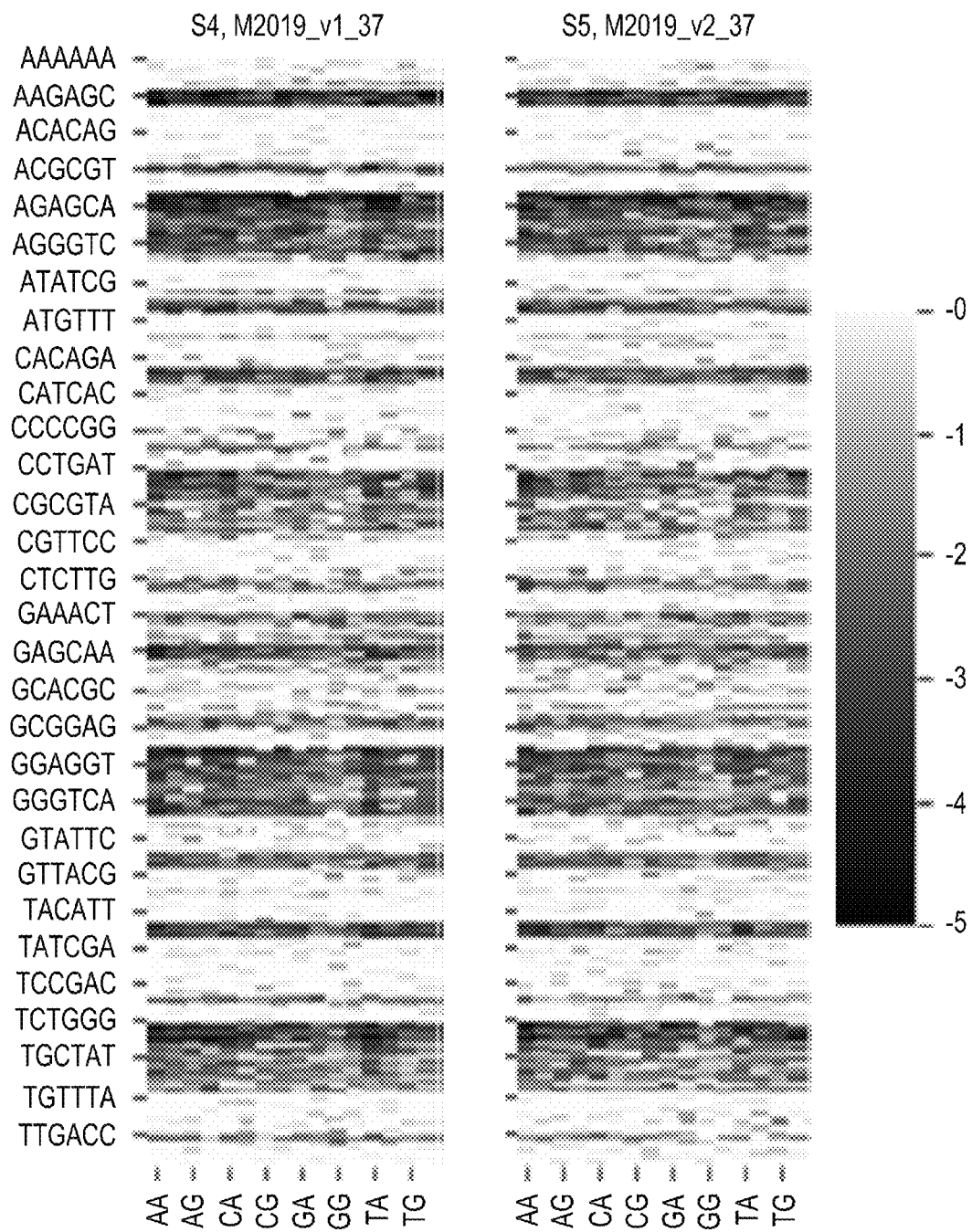
FIGS. 2A, 2B and 2C are heat maps showing the digestion patterns resulting from using the MAD2019 nuclease and three different guide RNAs with a plasmid target with degenerate PAM sequences at both 37° C. and 45° C.
Figure 2B:
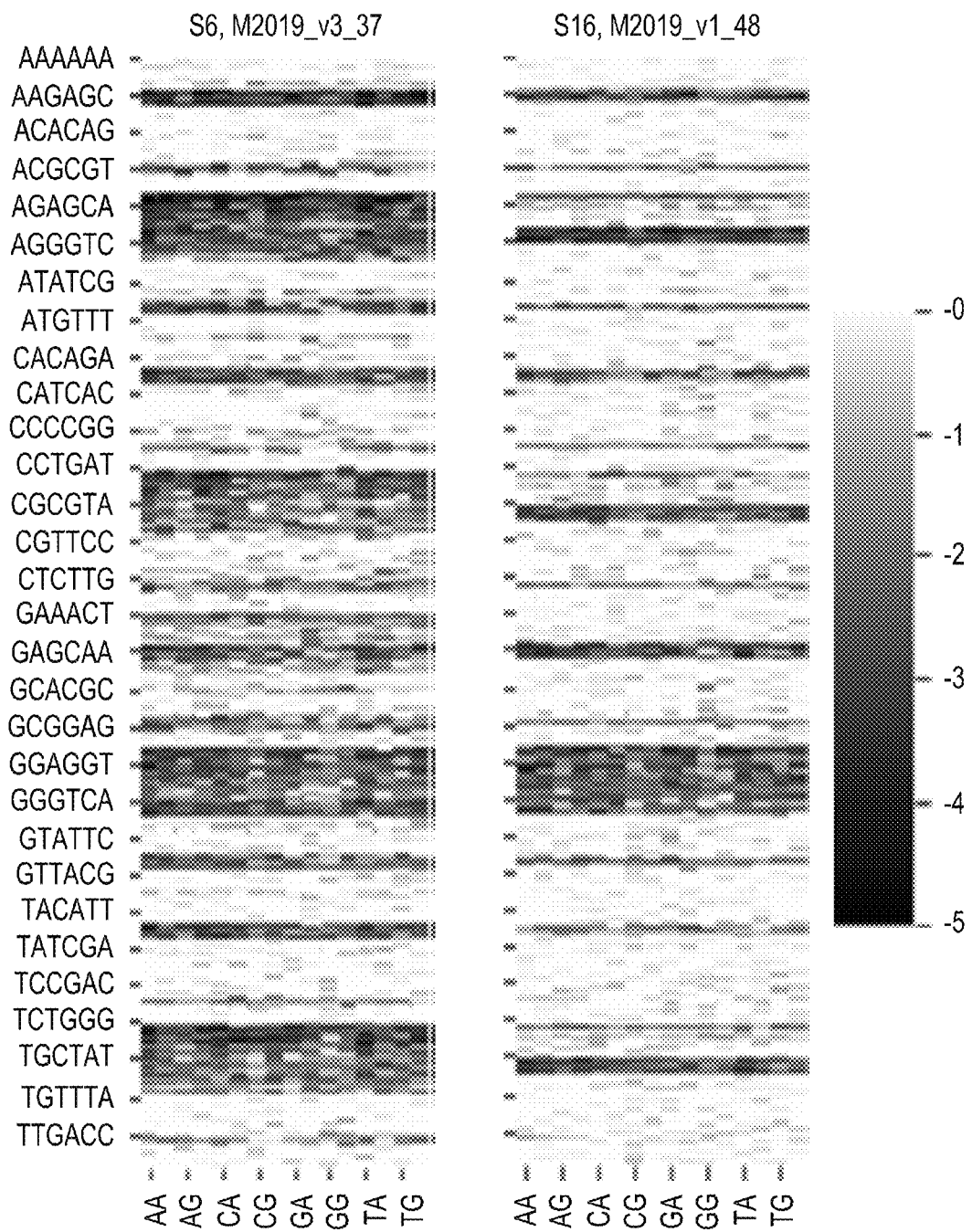
Figure 2C:
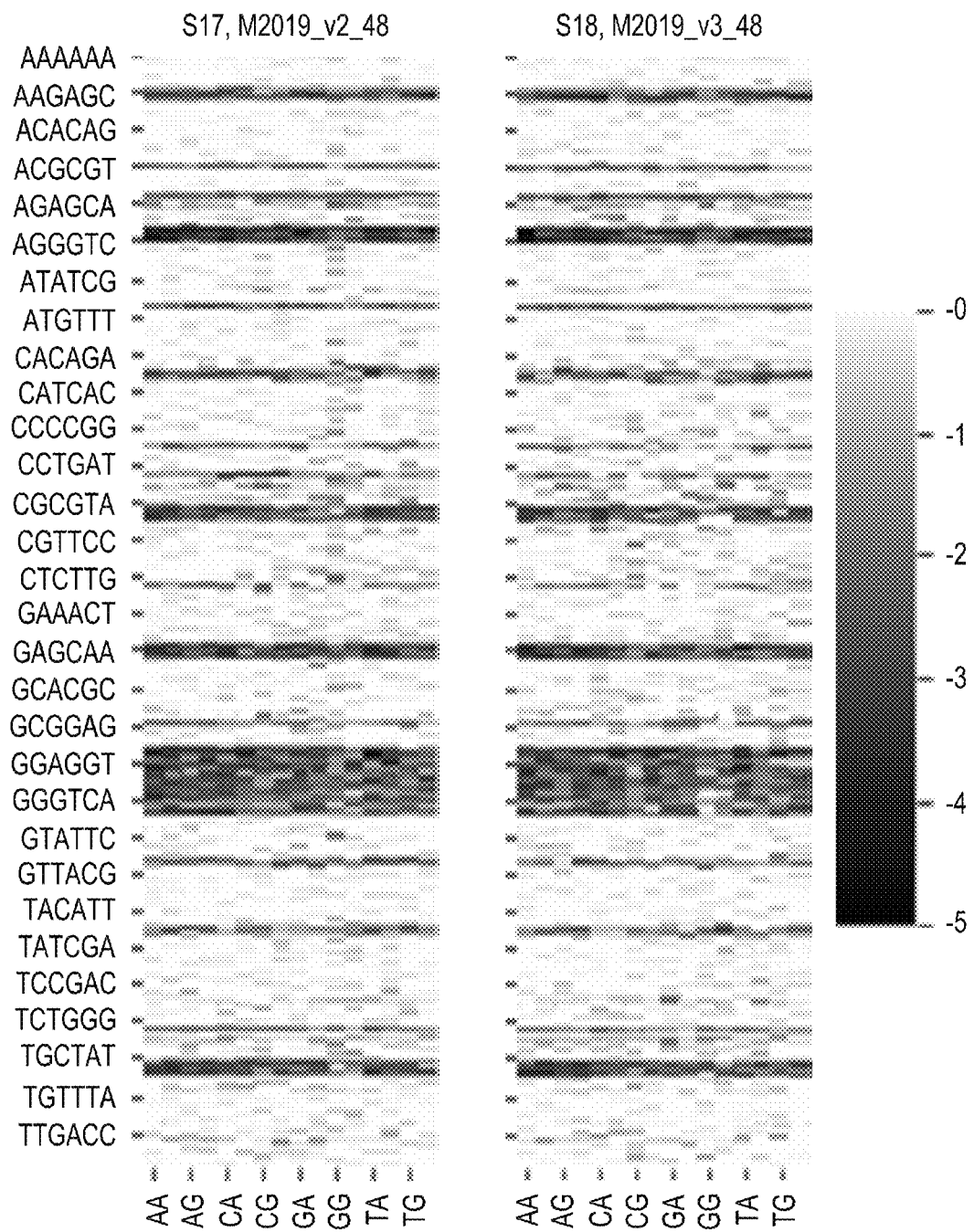

The MAD2019 nuclease and variant guide RNAs were produced in vitro to form RNP complexes (corresponding to step 113 of FIG. 1A) and the digestion patterns with a plasmid target, degenerate PAM sequences at two different temperatures (37° C. and 48° C.) were compared. The results are shown in FIGS. 2A-2C. There were no differences in performance in vitro between different variant sgRNAs used. An 8N degenerate PAM sequence was used in this assay. The Y-axis of FIGS. 2A-2C is for the first six nucleotides of the PAM and the two last nucleotides of the PAM are shown on the X-axis. A darker the color shows more depletion and higher activity.

MAD2017 Nuclease:

Three versions of sgRNA scaffolds were designed using the MAD2017 nuclease native CRISPR repeat and tracr RNA sequences (corresponding to step 107 of FIG. 1A). The native CRISPR repeat and tracr RNA for the MAD2017 nuclease (SEQ ID NOs: 12 and 13, respectively), as well as the variant gRNA scaffolds for MAD2017 (i.e., gRNA scaffold2017v2 [SEQ ID NO:14]; gRNA scaffold2017v3 [SEQ ID NO:15]; and gRNA scaffold 2017v4 [SEQ ID NO:16]) are shown in Table 3.

TABLE 3

First Round of Scaffold Optimization for MAD2017 Nickase

| Sequence Name | Sequence |
|---|---|
| Native CRISPR repeat MAD2017 | 5'-GTTTTAGAGCTGTGCTGTTTCGAATGGTTCCA AAAC-3' [SEQ ID NO: 12] |
| Native tracr RNA MAD2017 | 5'-TGTTGGAACTATTCGAAACAACACAGCGAGTT AAAATAAGGCTTTGTCCGTACACAACTTGTAAAAG GGGCACCCGATTCGGGTGCA-3' [SEQ ID NO: 13] |
| sgRNA 2017v2 | 5'-GTTTTAGAGCTGTGCTGTTTCGAAAAATCGAA ACAACACAGCGAGTTAAAATAAGGCTTTGTCCGTA CACAACTTGTAAAAGGGGCACCCGATTCGGGTGC-3' [SEQ ID NO: 14] |
| sgRNA 2017v3 | 5'-GTTTTAGAGCTGTGCTGTAAAAACAACACAGC GAGTTAAAATAAGGCTTTGTCCGTACACAACTTGT AAAAGGGGCACCCGATTCGGGTGC-3' [SEQ ID NO: 15] |
| sgRNA 2017v4 | 5'-GTTTTAGAGCTGTGCAAACACAGCGAGTTAAA ATAAGGCTTTGTCCGTACACAACTTGTAAAAGGGG CACCCGATTCGGGTGC-3' [SEQ ID NO: 16] |

Figure 3A:
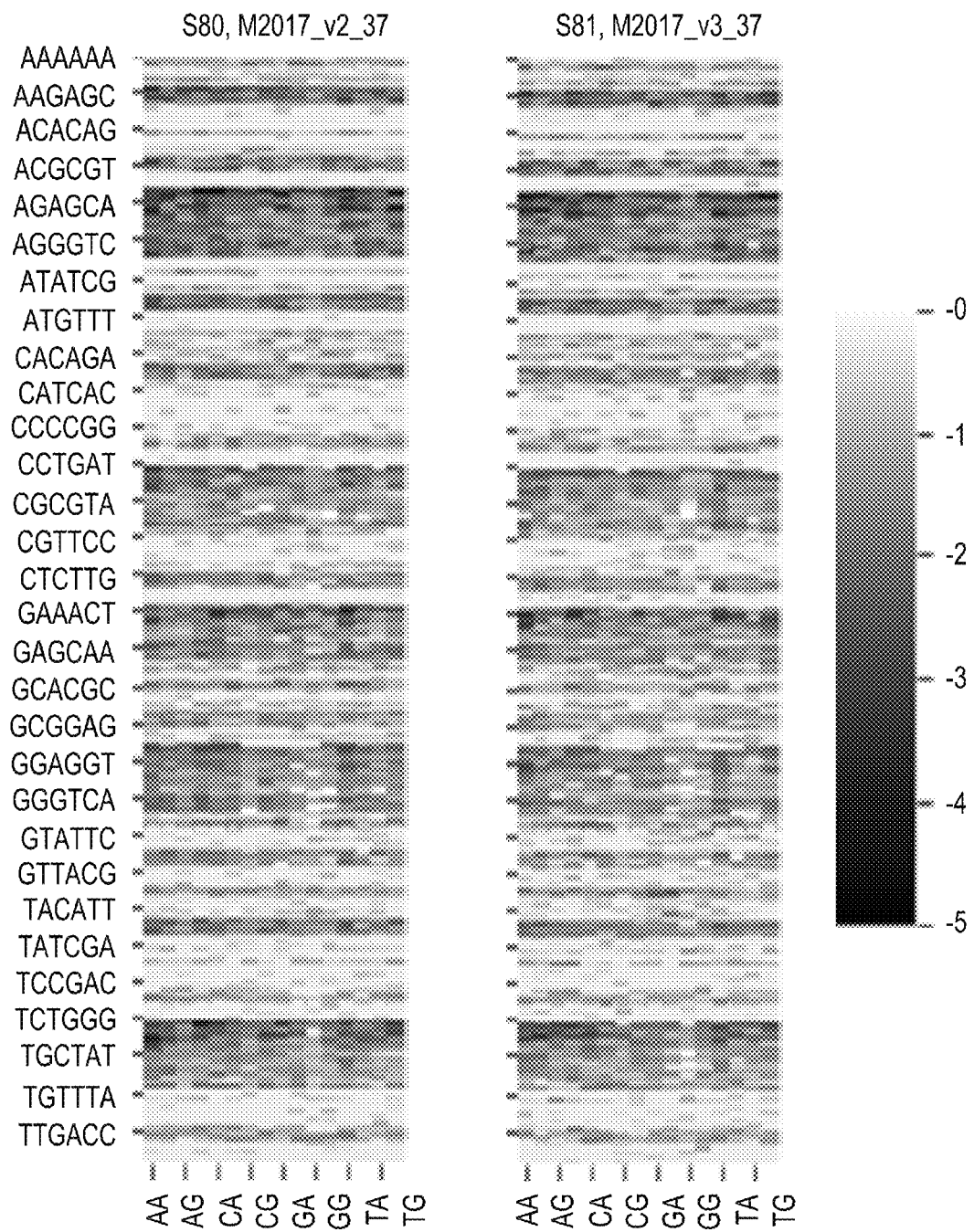
FIGS. 3A, 3B and 3C are heat maps showing the digestion pattern resulting from using the MAD2017 nuclease and three different guide RNAs with a plasmid target with degenerate PAM sequences at both 37° C. and 45° C.
Figure 3B:
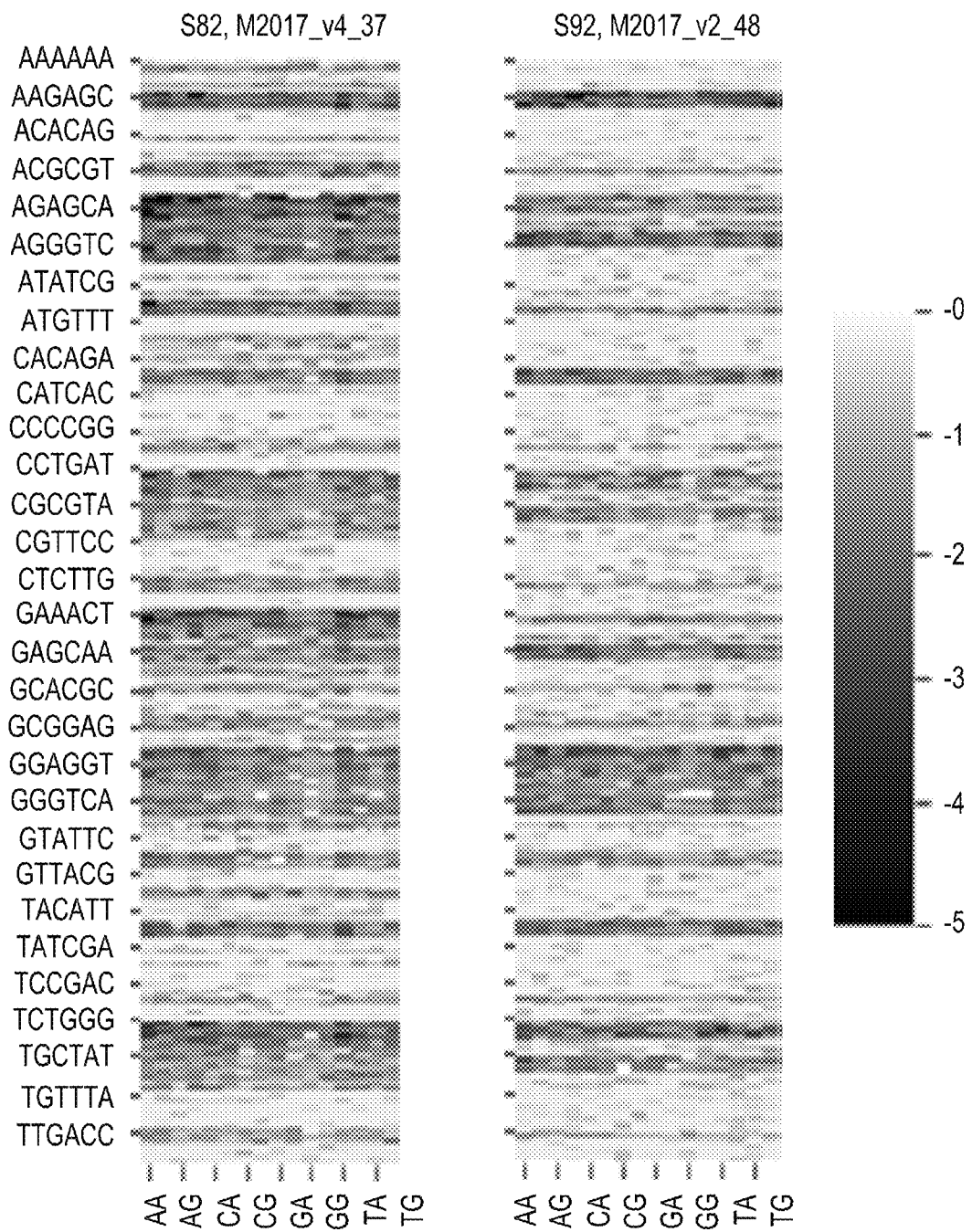
Figure 3C:
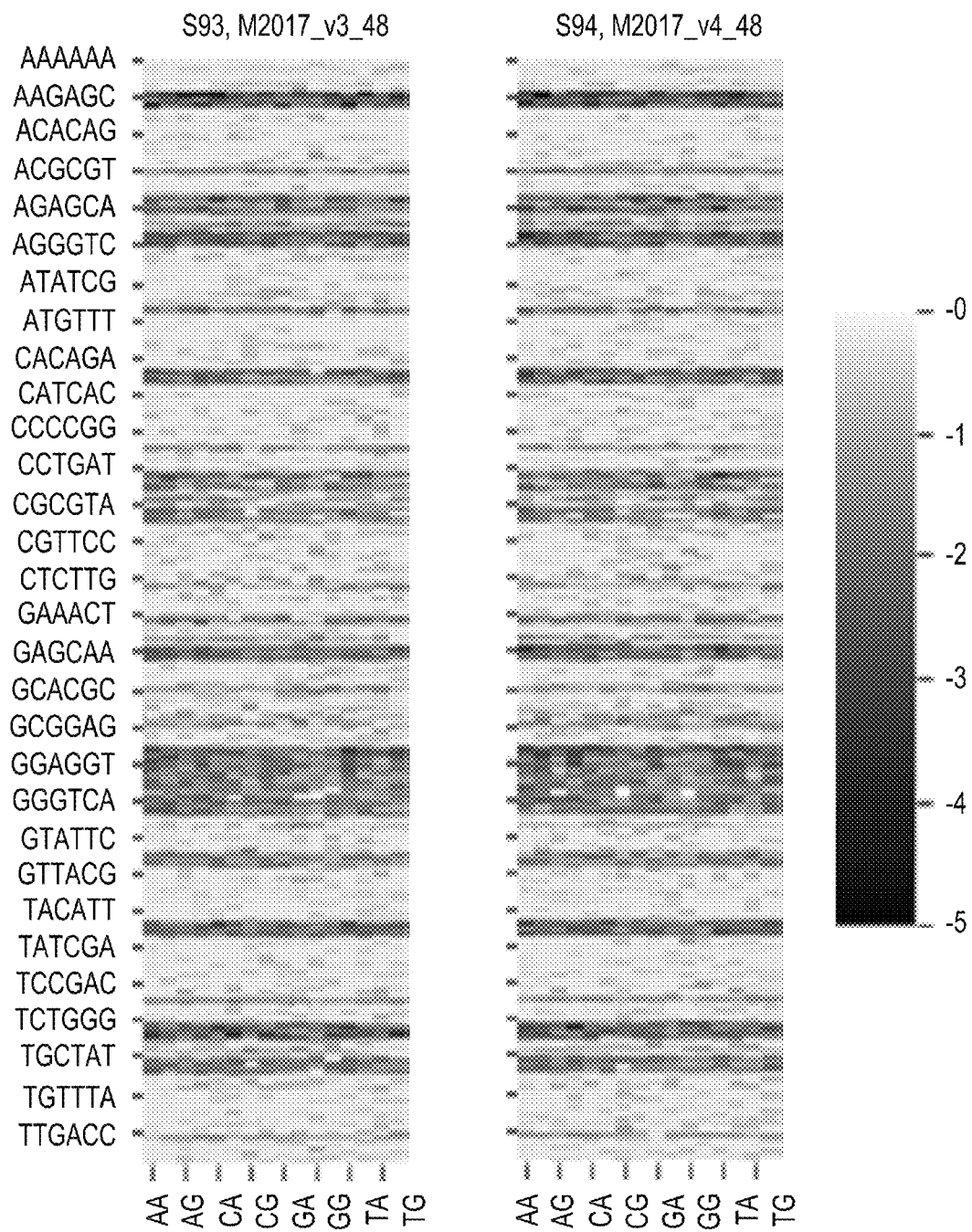

The MAD2017 nuclease and variant guide RNAs were produced in vitro to form RNP complexes (corresponding to step 113 of FIG. 1A) and the digestion patterns with a plasmid target, degenerate PAM sequences at two different temperatures (37° C. and 48° C.) were compared. The results are shown in FIGS. 3A-3C. There were no differences in performance in vitro between different variant sgRNAs used for the guide RNA production. An 8N degenerate PAM sequence was used in this assay. The Y-axis of FIGS. 3A-3C is for the first six nucleotides of the PAM and the two last nucleotides of the PAM are shown on the X-axis. A darker the color shows more depletion and higher activity.

In Vivo Test of Two Scaffolds:

A variant from the gRNA scaffolds listed in Tables 2 and 3 for each of MAD2019 and MAD2017 was used to test the effect on double strand break (DSB) formation activity on a GFP locus integrated in HEK293T cells. Three different guide lengths were tested (x-axis shown in FIGS. 4A and 4B), and two different guides (GFPg1 and GFPg5 in y-axis in FIGS. 4A and 4B) were used in different combinations. The sequences for GFPg1 and GFPg5 are shown in Table 4 below.

TABLE 4

Design of Full Guide: spacer + sgRNA scaffold + HR + G4

| Name of Guide | Guide Sequence | HR in CREATE fusion | G4 |
|---|---|---|---|
| GFPg1CF | GCTGAAGCAC TGCACGCCGT [SEQ ID NO: 28] | ACCCTCAGCCACGG CGTGCAGTGCTT [SEQ ID NO: 29] | ACTAACGGTGGTGG TGG [SEQ ID NO: 30] |
| GFPg5CF | GGTGCTGCTT CATGTGGTCG [SEQ ID NO: 31] | ACCCTCAGCCACGG CGTGCAGTGCTTCA GCCGCTATCCCGAC CACATGAAGCAG [SEQ ID NO: 32] | ACTAACGGTGGTGG TGG [SEQ ID NO: 30] |

Figure 4A:
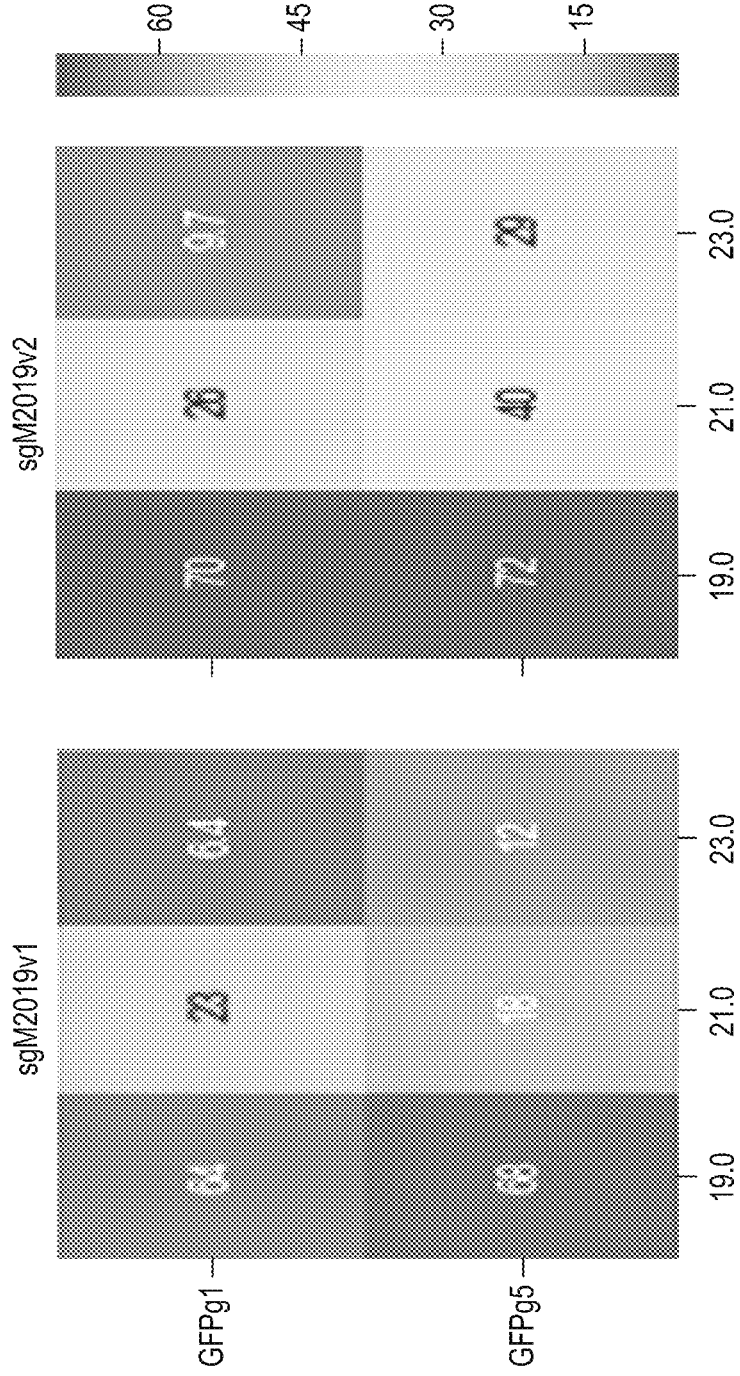
FIGS. 4A and 4B are heat maps showing the results where two sgRNA scaffolds for each of the MAD2019 and MAD107 nucleases were used to test double-strand break formation on a synthetic GFP locus integrated into HEK293T cells.
Figure 4B:
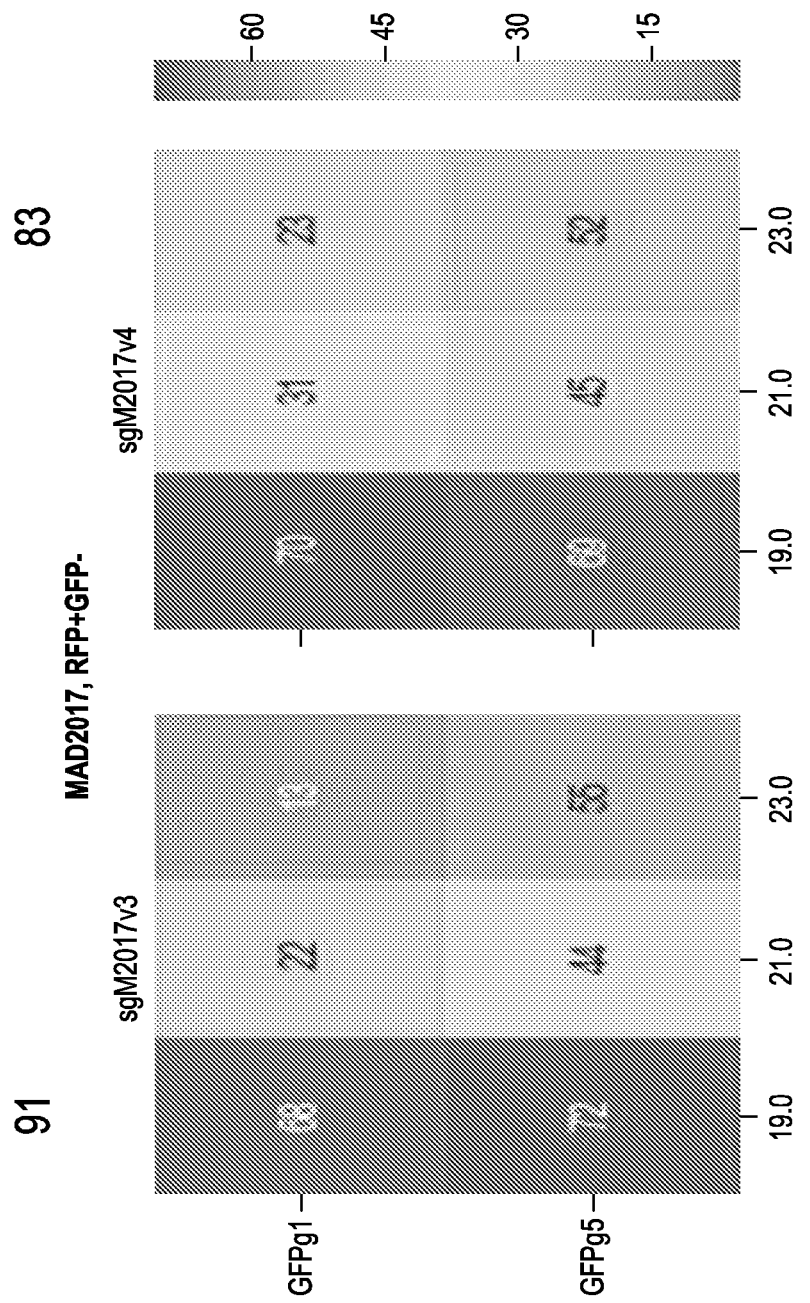

Two separate plasmids expressing either the MAD nuclease or a guide were transfected into the HEK293T cells with the integrated GFP locus. The coding sequences for the MAD nucleases were expressed under a CMV promoter cloned on a plasmid. The guides were produced from a separate plasmid expressed under the U6 promoter. The expression of the MAD nucleases was measured by an RFP signal produced as a T2A connected self-splicing protein fused to the carboxy terminus of the respective MAD nuclease. Double-strand break activity was measured from the population of HEK293T cells that retained RFP signal after transfection and expanded for 5-6 days. The results are shown in FIGS. 4A and 4B. For both the MAD2019 and MAD2017 nucleases, the 19-bp guides were the most efficient; and with this optimal guide length, there were no differences in cutting activity.

Figure 5A:
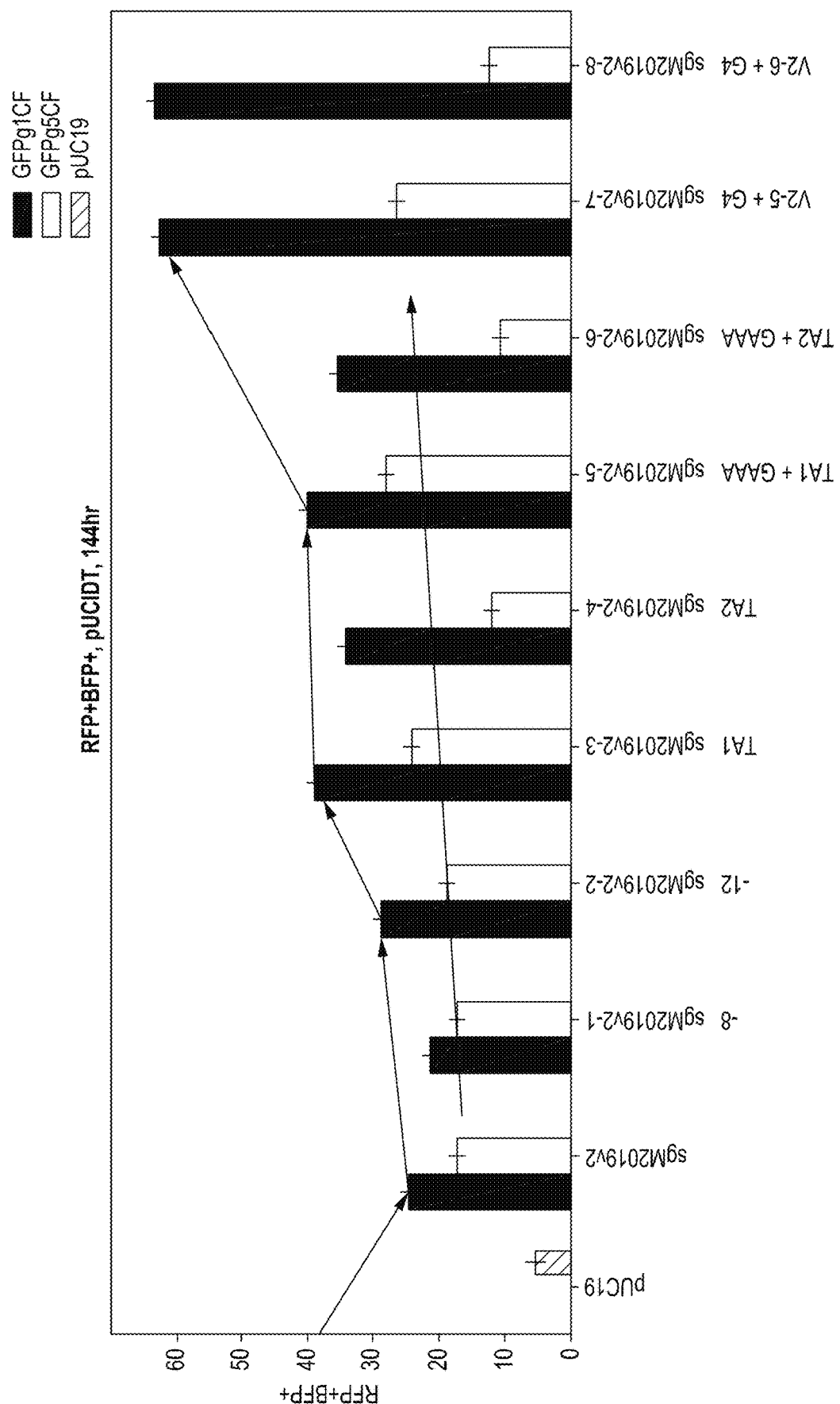
FIG. 5A shows the editing performance of the CF MAD2019 nickase and various scaffolds with two CREATE Fusion (CF) guides and FIG. 5B shows the cut performance of the MAD2019 nuclease and various scaffolds with two CREATE Fusion (CF) guides.
Figure 5B:
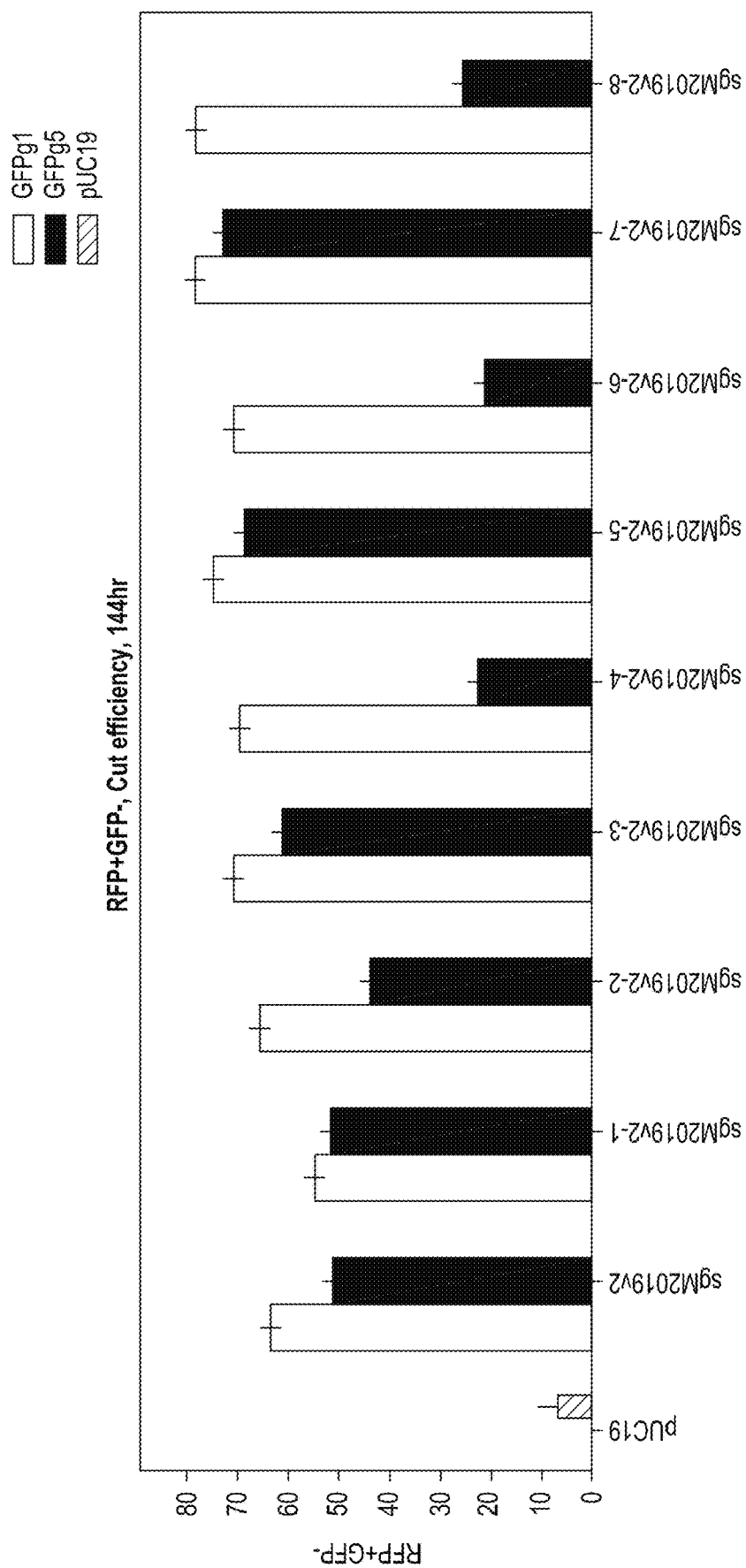

Further Optimization of sgRNA Scaffolds:

The MAD2019v2 sequence was used to further optimize the sgRNA scaffold. The sequence for each of these variants is shown in Table 5. The full guide comprised from 5' to 3': spacer+sgRNA scaffold (Table 5)+CF (HR in CREATE FUSION column in Table 4)+G4 (if included in the scaffold design) (also in Table 4). The guides were expressed under a U6 promoter. Editing performance using the MAD2019 nickase fused to a reverse transcriptase was measured by performing in vivo editing on the GFP locus in HEK293T cells changing GFP to BFP (see method depicted in FIG. 1B). The BFP signal was measured from cells maintaining an RFP signal after transfection. The results are shown in FIGS. 5A and 5B. In FIG. 5A, performance for each gRNA scaffold with the two different CF guides (GFPg1CF (dark bars) and GFPg5CF (light bars)) was measured. Improvement of performance is noticeable with GFPg1CF.

Cutting performance for each sRNA scaffold design with GFPg1CF (light bar) and GFPg5CF (medium dark bar) is shown in FIG. 5B. Cutting performance was measured with wildtype MAD2019 nuclease using the same guide designs used for the CF editing measured with the results shown in FIG. 5A.

TABLE 5

Second Round of Optimization for MAD2019 Nickase

| Sequence Name | Sequence |
|---|---|
| sgRNA 2019v2-1 | GTTTTAGAGCTGTGGAAATACAGCAAAGTTAAAATA AGGCTAGTCCGTATACAACGTGAAAACACGTGGCAC CGATTCGGTGC [SEQ ID NO: 17] |

TABLE 5-continued

Second Round of Optimization for MAD2019 Nickase

| Sequence Name | Sequence |
|---|---|
| sgRNA 2019v2-2 | GTTTTAGAGCTGGAAACAGCAAAGTTAAAATAAGGC TAGTCCGTATACAACGTGAAAACACGTGGCACCGAT TCGGTGC [SEQ ID NO: 18] |
| sgRNA 2019v2-3 | GTTTAAGAGCTGGAAACAGCAAAGTTTAAATAAGGC TAGTCCGTATACAACGTGAAAACACGTGGCACCGAT TCGGTGC [SEQ ID NO: 19] |
| sgRNA 2019v2-4 | GTTATAGAGCTGGAAACAGCAAAGTTATAATAAGGC TAGTCCGTATACAACGTGAAAACACGTGGCACCGAT TCGGTGC [SEQ ID NO: 20] |
| sgRNA 2019v2-5 | GTTTAAGAGCTGGAAACAGCAAAGTTTAAATAAGGC TAGTCCGTATACAACGTGGAAACACGTGGCACCGAT TCGGTGC [SEQ ID NO: 21] |
| sgRNA 2019v2-6 | GTTATAGAGCTGGAAACAGCAAAGTTATAATAAGGC TAGTCCGTATACAACGTGGAAACACGTGGCACCGAT TCGGTGC [SEQ ID NO: 22] |
| sgRNA 2019v2-7 | GTTTAAGAGCTGGAAACAGCAAAGTTTAAATAAGGC TAGTCCGTATACAACGTGGAAACACGTGGCACCGAT TCGGTGC [SEQ ID NO: 23] + G4 after CF (HR in CREATE FUSION) sequence |
| sgRNA 2019v2-8 | GTTATAGAGCTGGAAACAGCAAAGTTATAATAAGGC TAGTCCGTATACAACGTGGAAACACGTGGCACCGAT TCGGTGC [SEQ ID NO: 24] + G4 after CF (HR in CREATE FUSION) sequence |

Figure 6A:
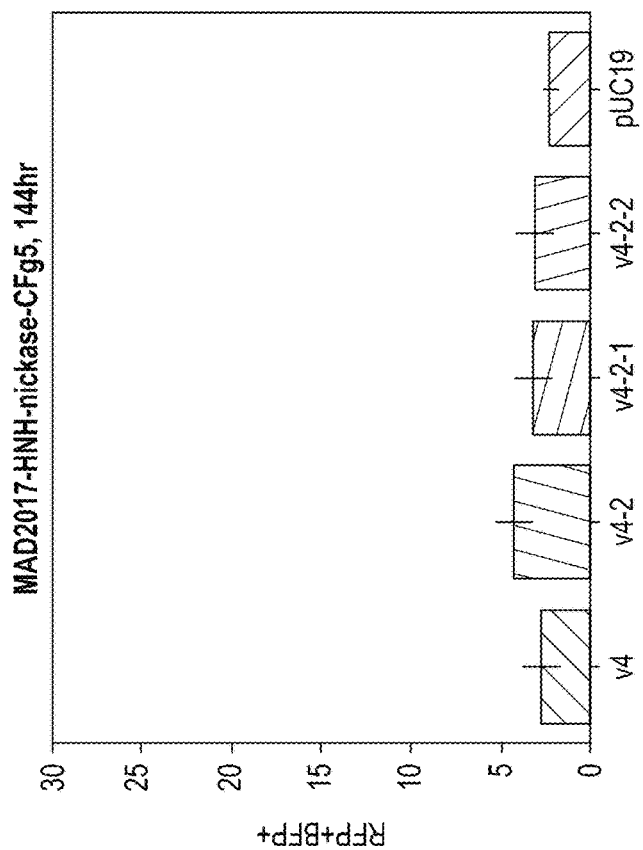
FIGS. 6A and 6B show the editing performance of CF MAD2017 nickase and various scaffolds with two CREATE Fusion (CF) guides.
Figure 6B:
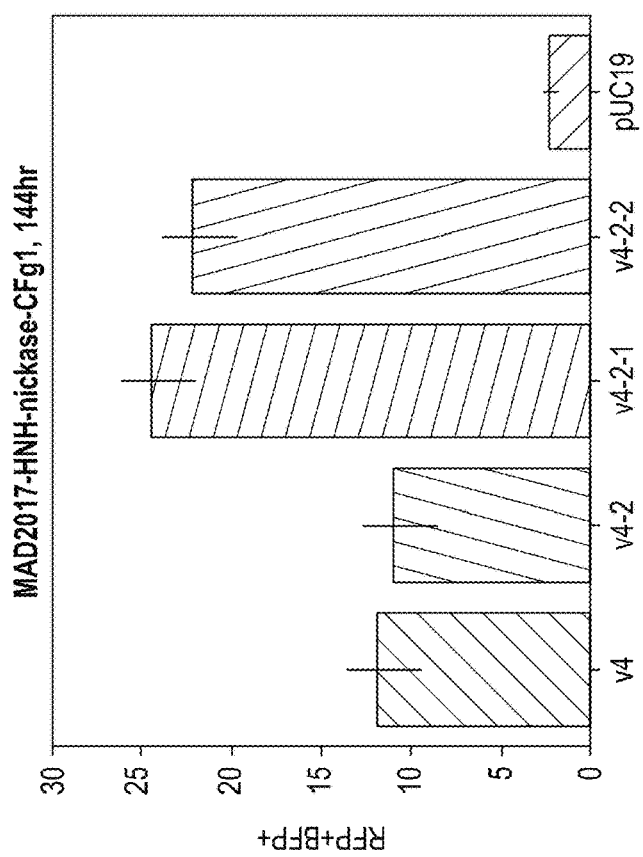
Figure 7B:
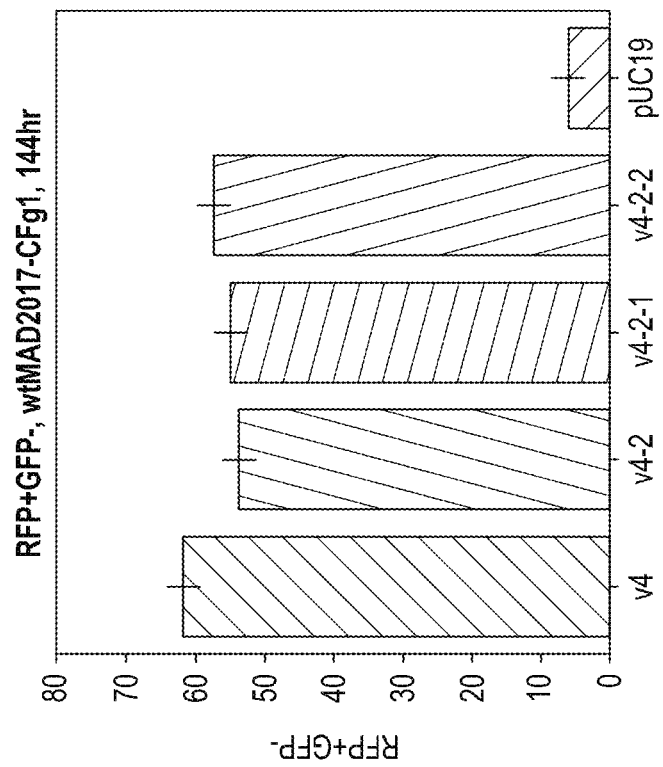
FIGS. 7A and 7B show the cut performance of MAD2017 nuclease and various scaffolds with two CREATE Fusion (CF) guides for cutting activity.
Figure 7A:
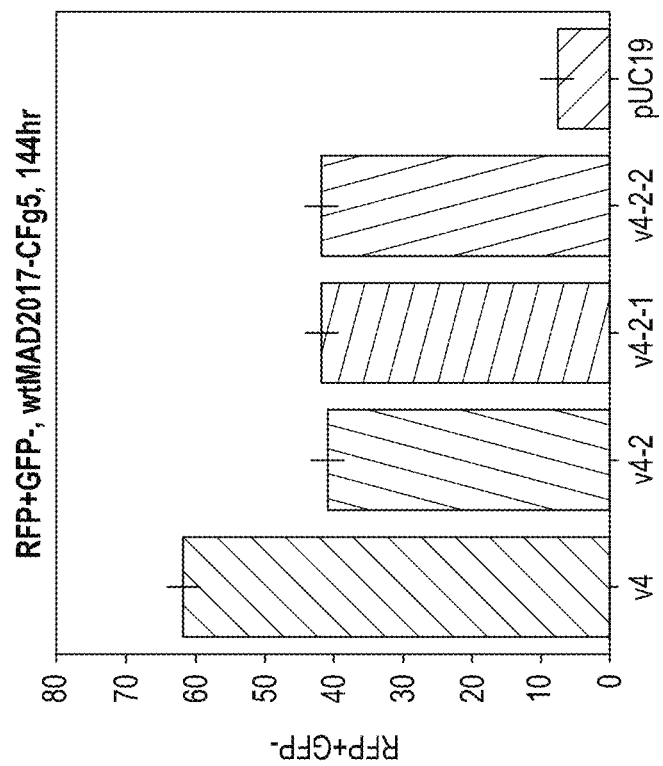

The AD2017v4 sequence was used to further optimize the gRNA scaffold. The sequences for each of these variants is shown in Table 6. The full guide comprised from 5' to 3': spacer+sgRNA scaffold (Table 6)+CF (HR in CREATE FUSION column in Table 4)+G4 (if included in the scaffold design) (also in Table 4). The guides were expressed under a U6 promoter. Editing performance using the MAD2017 nickase fused to a reverse transcriptase was measured by performing in vivo editing on the GFP locus in HEK293T cells changing GFP to BFP (see the method depicted in FIG. 1B). The BFP signal was measured from the cells maintaining an RFP signal after transfection. The results are shown in FIGS. 6A and 6B. Editing performance for each gRNA scaffold was greater for the CFg1 than for CFg5 (GFPg1CF (FIG. 6A) and GFPg5CF (FIG. 6B)); however, cut activity (FIGS. 7A and 7B, GFPg1CF and GFPg5CF, respectively) with the wildtype MAD2017 nuclease indicates the presence of G4 at the 3'-terminal of CF (HR) had the greatest effect. pUC 19 is an empty cloning vector that was used for a negative control for transfection.

TABLE 6

Second Round of Optimization for MAD2017 Nickase

| Sequence Name | Sequence |
|---|---|
| sgRNA 2017v4-2 | GTTTAAGAGCTGGAAACAGCGAGTTTAAATAAGGC TTTGTCCGTATACAACTTGTAAAAGGGGCACCCGA TTCGGGTGC [SEQ ID NO: 25] |
| sgRNA 2017v4-2-1 | GTTTAAGAGCTGGAAACAGCGAGTTTAAATAAGGC TTTGTCCGTATACAACTTGTAAAAGGGGCACCCGA TTCGGGTGC [SEQ ID NO: 26] + G4 after CF (HR in CREATE FUSION) sequence |

TABLE 6-continued

Second Round of Optimization for MAD2017 Nickase

| Sequence Name | Sequence |
|---|---|
| sgRNA 2017v4-2-2 | GTTTAAGAGCTGGAAACAGCGAGTTTAAATAAGGC TTTGTCCGTACACAACTTGAAAAAGGGGCACCCGA TTCGGGTGC [SEQ ID NO: 27] + G4 after CF (HR in CREATEFUSION) sequence |

Figure 8A:
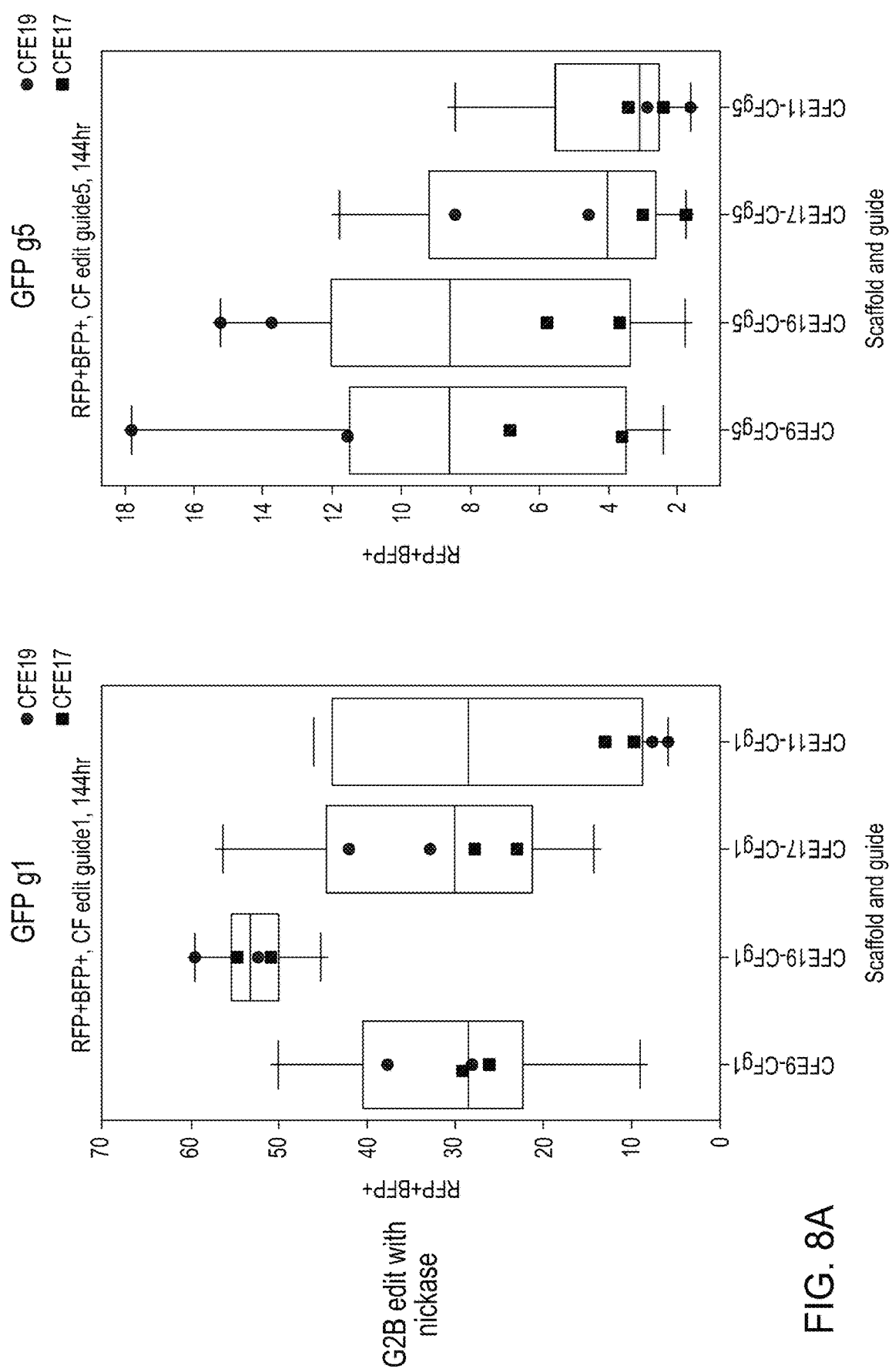
FIG. 8A shows GFP to BFP editing in HEK293T cells comprising an integrated GFP locus using the MAD2017 and MAD2019 nickases.
Figure 8B:
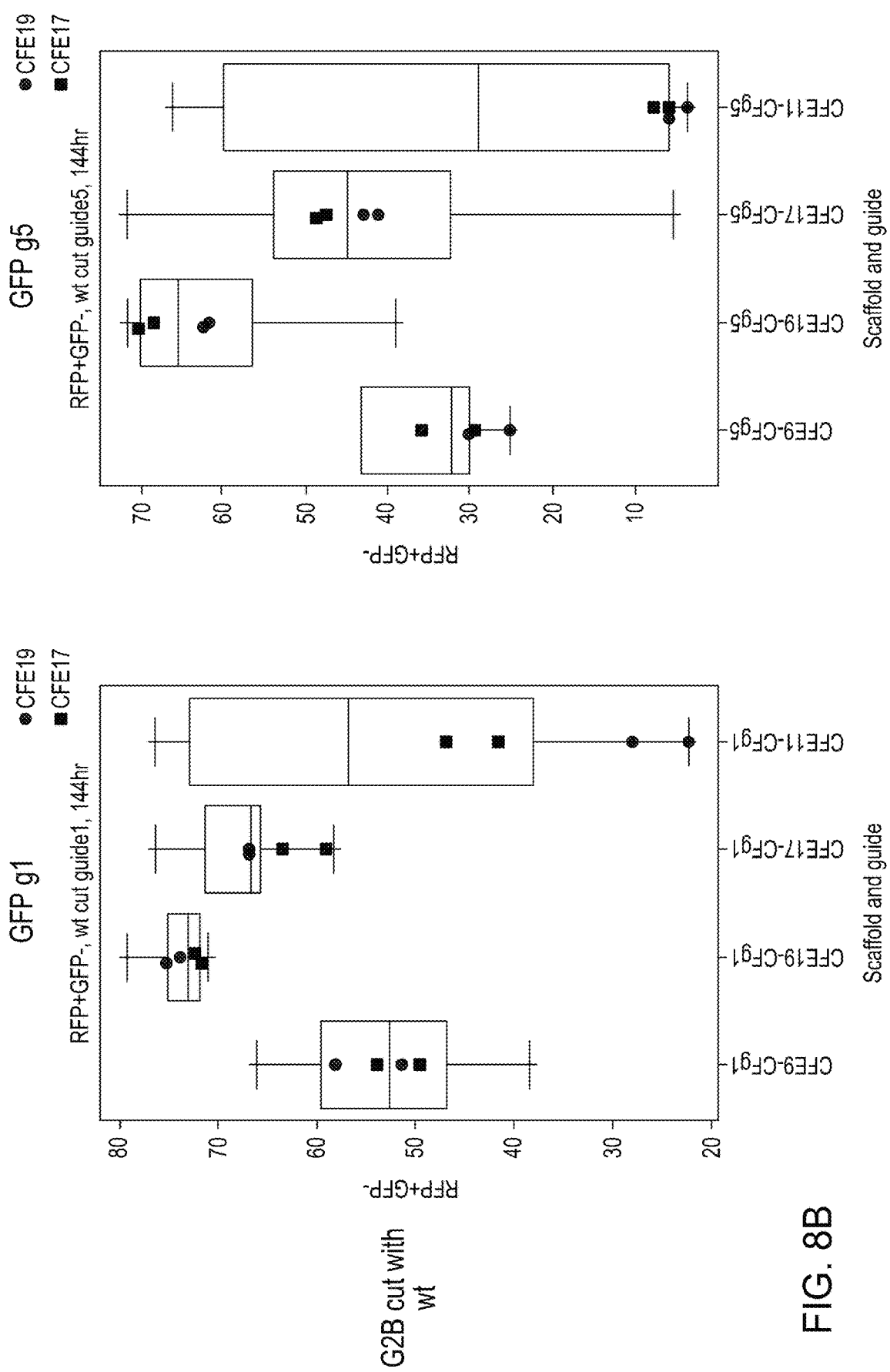
FIG. 8B shows GFP to GFP-cut activity in HEK293T cells with the MAD2017 and MAD2019 nucleases.

Scaffold compatibility between MAD nucleases showed that the gRNA scaffold for MAD2019 was the best universal scaffold for both MAD2019 and MAD2017 wild type and nickases. The results are shown in FIG. 8. FIG. 8A shows GFP to BFP CF editing in HEK293T cells with an integrated GFP locus (GFPg1, left top graph and GFPg5, right top graph). FIG. 8B shows GFP to GFP-cut activity in HEK293T cells with the MAD2019 and MAD2017 nucleases. CFE19-CFg1 had the best universal performance.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶16.

We claim:

1. A nucleic acid-guided nickase selected from the following nickases: MAD2019-H848A, having the amino acid sequence of SEQ ID NO: 3; and MAD2019-N871A, having the amino acid sequence of SEQ ID NO: 4.

2. The nickase of claim 1 having the amino acid sequence of SEQ ID NO: 3.

3. The nickase of claim 1 having the amino acid sequence of SEQ ID NO: 4.

4. The nickase of claim 1 having an amino acid sequence of SEQ ID NO: 3, in a nucleic acid-guided nickase editing system with a gRNA scaffold having a nucleic acid sequence of SEQ ID NO: 9, SEQ ID NO: 10, SEQ ID NO: 11, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

5. The nickase of claim 4 having an amino acid sequence of SEQ ID NO: 3, in the nucleic acid-guided nickase editing system with a gRNA scaffold having a nucleic acid sequence of SEQ ID NO: 9.

6. The nickase of claim 4 having an amino acid sequence of SEQ ID NO: 3, in the nucleic acid-guided nickase editing system with a gRNA scaffold having a nucleic acid sequence of SEQ ID NO: 10.

7. The nickase of claim 4 having an amino acid sequence of SEQ ID NO: 3, in the nucleic acid-guided nickase editing system with a gRNA scaffold having a nucleic acid sequence of SEQ ID NO: 11.

8. The nickase of claim 4 having an amino acid sequence of SEQ ID NO: 3, in the nucleic acid-guided nickase editing system with a gRNA scaffold having a nucleic acid sequence of SEQ ID NO: 17.

9. The nickase of claim 4 having an amino acid sequence of SEQ ID NO: 3, in the nucleic acid-guided nickase editing system with a gRNA scaffold having a nucleic acid sequence of SEQ ID NO: 18.

10. The nickase of claim 4 having an amino acid sequence of SEQ ID NO: 3, in the nucleic acid-guided nickase editing system with a gRNA scaffold having a nucleic acid sequence of SEQ ID NO: 19.

11. The nickase of claim 4 having an amino acid sequence of SEQ ID NO: 3, in the nucleic acid-guided nickase editing system with a gRNA scaffold having a nucleic acid sequence of SEQ ID NO: 20.

12. The nickase of claim 4 having an amino acid sequence of SEQ ID NO: 3, in the nucleic acid-guided nickase editing system with a gRNA scaffold having a nucleic acid sequence of SEQ ID NO: 21.

13. The nickase of claim 4 having an amino acid sequence of SEQ ID NO: 3, in the nucleic acid-guided nickase editing system with a gRNA scaffold having a nucleic acid sequence of SEQ ID NO: 22.

14. The nickase of claim 4 having an amino acid sequence of SEQ ID NO: 3, in the nucleic acid-guided nickase editing system with a gRNA scaffold having a nucleic acid sequence of SEQ ID NO: 23.

15. The nickase of claim 1 having an amino acid sequence of SEQ ID NO: 3, in the nucleic acid-guided nickase editing system with a gRNA scaffold having a nucleic acid sequence of SEQ ID NO: 24.

16. The nickase of claim 1 having an amino acid sequence of SEQ ID NO: 4, in a nucleic acid-guided nickase editing system with a gRNA scaffold having a nucleic acid sequence of SEQ ID NO: 9, SEQ ID NO: 10, SEQ ID NO: 11, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

17. The nickase of claim 16 having an amino acid sequence of SEQ ID NO: 4, in the nucleic acid-guided nickase editing system with a gRNA scaffold having a nucleic acid sequence of SEQ ID NO: 9.

18. The nickase of claim 16 having an amino acid sequence of SEQ ID NO: 4, in the nucleic acid-guided nickase editing system with a gRNA scaffold having a nucleic acid sequence of SEQ ID NO: 10.

19. The nickase of claim 16 having an amino acid sequence of SEQ ID NO: 4, in the nucleic acid-guided nickase editing system with a gRNA scaffold having a nucleic acid sequence of SEQ ID NO: 11.

20. The nickase of claim 16 having an amino acid sequence of SEQ ID NO: 4, in the nucleic acid-guided nickase editing system with a gRNA scaffold having a nucleic acid sequence of SEQ ID NO: 17.

21. The nickase of claim 16 having an amino acid sequence of SEQ ID NO: 4, in the nucleic acid-guided nickase editing system with a gRNA scaffold having the nucleic acid sequence of SEQ ID NO: 18.

22. The nickase of claim 16 having an amino acid sequence of SEQ ID NO: 4, in the system with a gRNA scaffold having a nucleic acid sequence of SEQ ID NO: 19.

23. The nickase of claim 16 having an amino acid sequence of SEQ ID NO: 4, in the system with a gRNA scaffold having a nucleic acid sequence of SEQ ID NO: 20.

24. The nickase of claim 16 having an amino acid sequence of SEQ ID NO: 4, in the system with a gRNA scaffold having a nucleic acid sequence of SEQ ID NO: 21.

25. The nickase of claim 16 having an amino acid sequence of SEQ ID NO: 4, in the system with a gRNA scaffold having a nucleic acid sequence of SEQ ID NO: 22.

26. The nickase of claim 16 having an amino acid sequence of SEQ ID NO: 4, in the system with a gRNA scaffold having a nucleic acid sequence of SEQ ID NO: 23.

27. The nickase of claim 16 having an amino acid sequence of SEQ ID NO: 4, in the system with a gRNA scaffold having a nucleic acid sequence of SEQ ID NO: 24.

28. The nickase of claim 1 having an amino acid sequence of SEQ ID NO: 3, in a nucleic acid-guided nickase editing system with a native CRISPR repeat having a nucleic acid sequence of SEQ ID NO: 7 and a native tracr RNA having a nucleic acid sequence of SEQ ID NO:8.

29. The nickase of claim 1 having an amino acid sequence of SEQ ID NO: 4, in a nucleic acid-guided nickase editing system with a native CRISPR repeat having a nucleic acid sequence of SEQ ID NO: 7 and a native tracr RNA having a nucleic acid sequence of SEQ ID NO:8.

30. The nickase of claim 1 having an amino acid sequence of SEQ ID NO: 3 or SEQ ID NO; 4, in a nucleic acid-guided nickase editing system comprising a guide RNA wherein the guide comprises from 5' to 3' a guide sequence, a homology region and SEQ ID NO: 30.

\* \* \* \* \*